United States Patent [19]

Anderson

[11] Patent Number: 5,238,613
[45] Date of Patent: Aug. 24, 1993

[54] MICROPOROUS MATERIALS

[76] Inventor: David M. Anderson, 337 Squire Hall, S.U.N.Y., Buffalo, N.Y. 14114

[21] Appl. No.: 835,019

[22] Filed: Feb. 12, 1992

Related U.S. Application Data

[63] Continuation of Ser. No. 500,213, Mar. 27, 1990, abandoned, which is a continuation of Ser. No. 52,713, May 20, 1987, abandoned.

[51] Int. Cl.$^5$ .............................................. B01D 69/00
[52] U.S. Cl. .................. 264/22; 210/500.27; 210/500.35
[58] Field of Search ............... 210/500.35, 500.27, 210/500.23; 264/41, 49, 22

[56] References Cited

U.S. PATENT DOCUMENTS

| | | | |
|---|---|---|---|
| 3,956,020 | 5/1976 | Weininger et al. | 264/49 |
| 4,177,150 | 12/1979 | Inoue et al. | 210/500.36 |
| 4,415,615 | 11/1983 | May et al. | 427/54.1 X |
| 4,519,909 | 5/1985 | Castro | 210/500.27 |
| 4,539,256 | 9/1985 | Shipman | 264/41 |

*Primary Examiner*—Frank Spear
*Attorney, Agent, or Firm*—Blodgett & Blodgett

[57] ABSTRACT

A new type of polymeric microporous membrane has been synthesized which is distinguished by a highly-branched porespace morphology that is continuous and triply-periodic, and thus very precisely controlled and easily characterized. The membrane consists of a polymeric matrix containing pores of diameter on the order of 10 nm connected into a continuous pore network exhibiting long-range three-dimensional order. This long-range order is evidenced in small-angle X-ray scattering (SAXS) experiments by Bragg reflections that index to a triply-periodic space group, as well as in electron micrographs that match predictions from a theoretical model of the same space group and lattice parameter. The membrane combines three important features that have not been present simultaneously in any prior art membrane having pore diameters between 2 nm and 1 micron. First, the pores are identical in size and shape to a very high degree, and their size can be controlled in the synthesis. Second, the porespace is characterized by intricate branching and reconnections, with at least three pore throats meeting at a given pore body, this number (the coordination number) being the same for each pore body, and the porespace is isotropic in the cases where the space group is cubic. These two features allow accurately controlled sieving on the basis of particle size and shape, and provide highly accessible and precisely shaped pore bodies and surfaces for other applications such as catalysis, ion exchange, and the preparation of metal microstructures. And third, the membrane has a high porosity (approximately 90%).

9 Claims, 8 Drawing Sheets

FIG. 7

Equation 1

$$F_L = \frac{1}{2c} \sum \sum_{q_{bj}} \left\{ \hat{S}^{-1}(q_{bj}) - \frac{1}{2N^2 f(1-f)} \left[ \frac{q_{bj}^2 N}{2} + \frac{S(f)}{f(1-f)} \right] \right\} \hat{\psi}_{q_{bj}} \hat{\psi}_{-q_{bj}}$$

Equation 2

$$\psi_{\underline{q}} = \iiint_V e^{i\underline{q}\cdot\underline{r}} d^3\underline{r} = \frac{i}{q^2} \iint_{\partial V} \underline{n} \cdot \underline{q} \, e^{i\underline{q}\cdot\underline{r}} \, dA$$

Equation 3

$$\frac{M}{q^2} \left\{ \left[ \cos(a+b) - \cos(a+c) \right]/b(c-b) - \left[ \cos a - \cos(a+c) \right]/bc \right\},$$

where $a = (x_1, y_1, z_1) \cdot \underline{q}$, $b = (x_2 - x_1, y_2 - y_1, z_2 - z_1) \cdot \underline{q}$, $c = (x_3, y_3, z_3) \cdot \underline{q} - a$, $M = |(x_2 - x_1, y_2 - y_1, z_2 - z_1) \times (x_3 - x_1, y_3 - y_1, z_3 - z_1)|.$

MICROPOROUS MATERIALS

This is a continuation of copending application Ser. No. 07/500,213 filed on Mar. 27, 1990, which is a continuation of application Ser. No. 07/052,713, filed May 20, 1987, now abandoned.

FIELD OF THE INVENTION

The present invention is in the field of microporous membrane materials, especially polymeric membranes.

The past 20 years has seen tremendous growth in the applications of polymeric membranes, not only in filtration—microfiltration (MF), ultrafiltration (UF), and hyperfiltration or reverse osmosis (RO)—but also in a variety of other areas such as fuel cells and batteries, controlled-release devices as for drug or herbicide metering, dialysis and electrodialysis, pervaporation, electrophoresis, membrane reactors, ion-selective electrodes, and as supports for liquid membranes, to name some important areas. Furthermore, modification of neutral polymer membranes can yield ionomeric or 'ion-exchange' membranes which are finding increasing application in many chemical, electrochemical, filtration and even biochemical processes. In many applications the availability of a membrane with precisely-controlled porespace and high porosity would represent a significant technological advance.

BACKGROUND ART

The ultimate membrane would have identical, highly interconnected pores comprising a porespace with perfect three-dimensional periodic order. This ideal has been approached in the development of polymeric microporous membranes but never achieved. The simplest type of sieve is a net filter, where each layer in the filter is a woven mesh. The geometry of the pore space in a given layer is thus a close approximation to a finite portion of a doubly-periodic net, the latter being a mathematical idealization with perfect regularity within the plane. Note that if, in addition, these doubly-periodic layers are stacked at regular intervals with all layers in vertical registry, the resulting sieve is triply-periodic. Woven mesh filters are not available with pore sizes less than about 60 microns, so they cannot be used for reverse osmosis, ultrafiltration, nor even microfiltration.

Another doubly-periodic geometry that is achieved in some filters is that of hexagonally close-packed cylindrical pores. For example, glass capillary bundle filters are made from close-packed arrays of parallel glass capillaries. Capillary arrays can also be formed from hollow fibres of organic polymers, although these are not yet available commercially. A major drawback of cylindrical-pore filters is the lack of porespace branchings and reconnections, which leaves only one pathway for a fluid particle entering a given pore; thus clogging becomes a serious problem, as does sensitivity to handling. Of course, cylindrical pores can provide a narrow distribution of pore sizes without necessarily lying on a doubly-periodic lattice; for example, nucleation-track filters have randomly placed parallel cylindrical pores. But this randomness means that the number of pores per unit cross-sectional area must be kept small to maintain monodispersity, so that these filters have the additional drawback of low porosity and thus low filtration rates. Nevertheless, nucleation-track filters are considered the best membrane filters available for sieving below 60 microns, despite these obvious drawbacks.

U.S. Pat. No. 4,280,909 describes a microporous membrane which is, strictly speaking, triply-periodic, but the topology of the porespace is exactly the same as in the capillary array membranes, namely the flow channels are strictly linear and there are no porespace branchings or reconnections. The periodicity in the third dimension refers only to the vertical stacking of tapered pores of equal height, so that the cylindrical pores of the capillary array membrane have become instead tubular pores with a periodically varying diameter. This membrane does not satisfy one of the most important desired features, namely the intricate yet controlled porespace. A precisely defined porespace with branching and reconnections, in which each identical pore body connects to exactly the same number of other pore bodies through identical pore throats, is important in:

a) reducing clogging, as when the membrane is used for filtration, for example;

b) enhancing mixing, as when the membrane is used in catalysis or ion exchange, for example; and, c) providing accessible channels and pore bodies of specific shape, as when the membrane is used in the preparation of metal microstructures [Jacobs et al. 1982], for example.

Sintered-particle membranes have intricate three-dimensional porespaces with many interconnections, but have oddly-shaped and polydisperse pores as well as low pore density, the latter drawback being the primary reason they have been generally replaced by membrane filters. Most sintered-particle filters have retention ratings at or above 0.7 microns.

The membrane that is most commonly used in particle filtration has high porosity but a random, irregular porespace that makes it generally unusable as a sieve. Distributions of pore radii in cellulose nitrate membrane filters have been measured using mercury porisimetry, and the distributions are very broad: the full-width at half-maximum (FWHM) of the distribution is about equal to the average radius [Brock 1983].

In the realm of nonpolymeric sieves, zeolites provide fairly well-controlled, triply-periodic pore networks, but the free diameters of aperatures governing access to channels are generally less than 2 nm, and in fact nearly always less than 1 nm [Barrer 1978]; also the porosities of zeolites (defined as cc's of water per cc of crystal) are nearly always less than 50% Furthermore, most zeolites selectively absorb polar molecules because most are themselves highly polar, having high local electrostatic fields and field gradients [Barrer 1978]. Perhaps most importantly, the macroscopic size of zeolite crystals has very serious practical limitations making such materials unsuitable for forming reasonably large membrane-like structures with the necessary degree of continuity.

These and other difficulties with prior materials and methods have been obviated in a novel and inventive manner by the present invention.

SUMMARY OF THE INVENTION

The invention involves a polymeric, microporous membrane material characterized by a continuous, triply-periodic, highly branched and interconnected pore space morphology having a globally uniform, pre-selected pore size. The pore size ranges from two nanometers to sixty microns, preferably in the range of two nanometers to one micron and particularly preferably on the order of ten nanometers. The material of the invention is characterized by high porosity: greater than fifty percent and, for certain applications, greater than ninety percent. The invention involves controlled variation of the pore characteristics, particularly the electrochemical characteristics.

The invention involves several related methods for forming microporous membrane materials, including polymerization of the hydrophobic component in a ternary surfactant/water/hydrophobe cubic phase, and other thermodynamically stable or metastable phases of phase-segregated systems, especially systems which are substantially ternary or binary.

The model used was determined by the constant-mean-curvature surface of the 'D' family (Pn3m symmetry) which matches the volume fractions of the sample. A computer was used to send projection rays through the theoretical model, and the grey level at each pixel calculated.

Figure 5A:
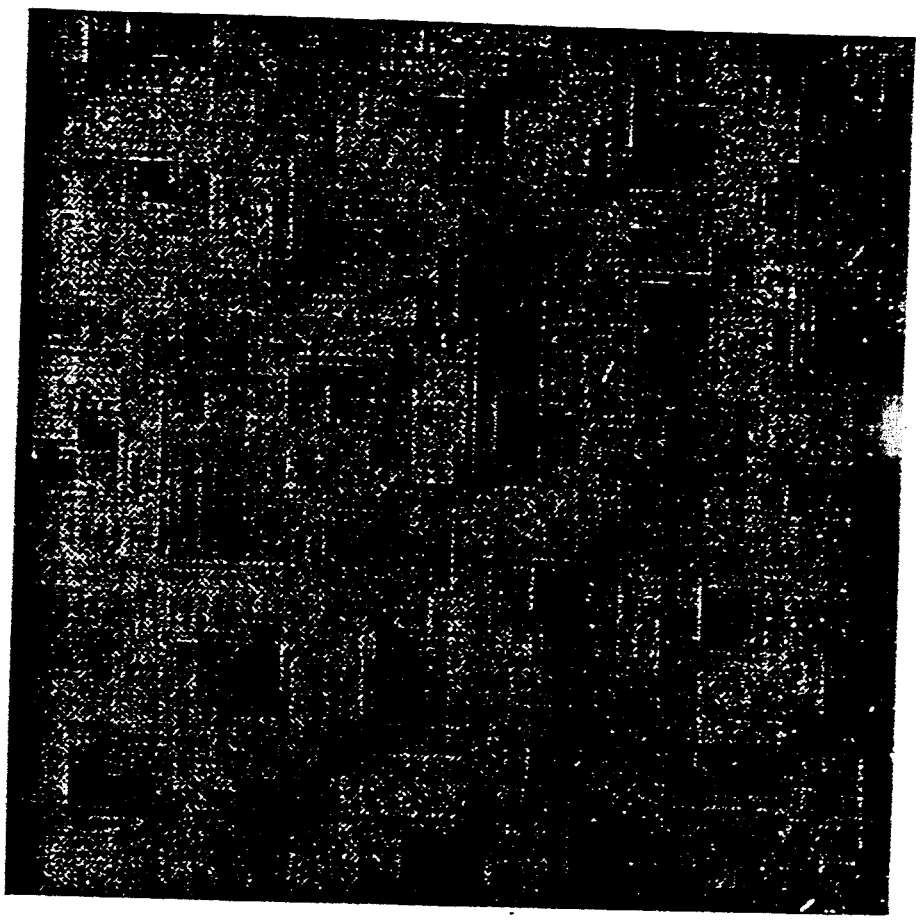
FIG. 5 A and B show digitized electron micrograph of:
  A) a bicontinuous cubic phase in a star-block PI/PS copolymer, and
  B) a prediction using a bicontinuous model from the applicant's doctoral thesis, Anderson, 1986.
Figure 5B:
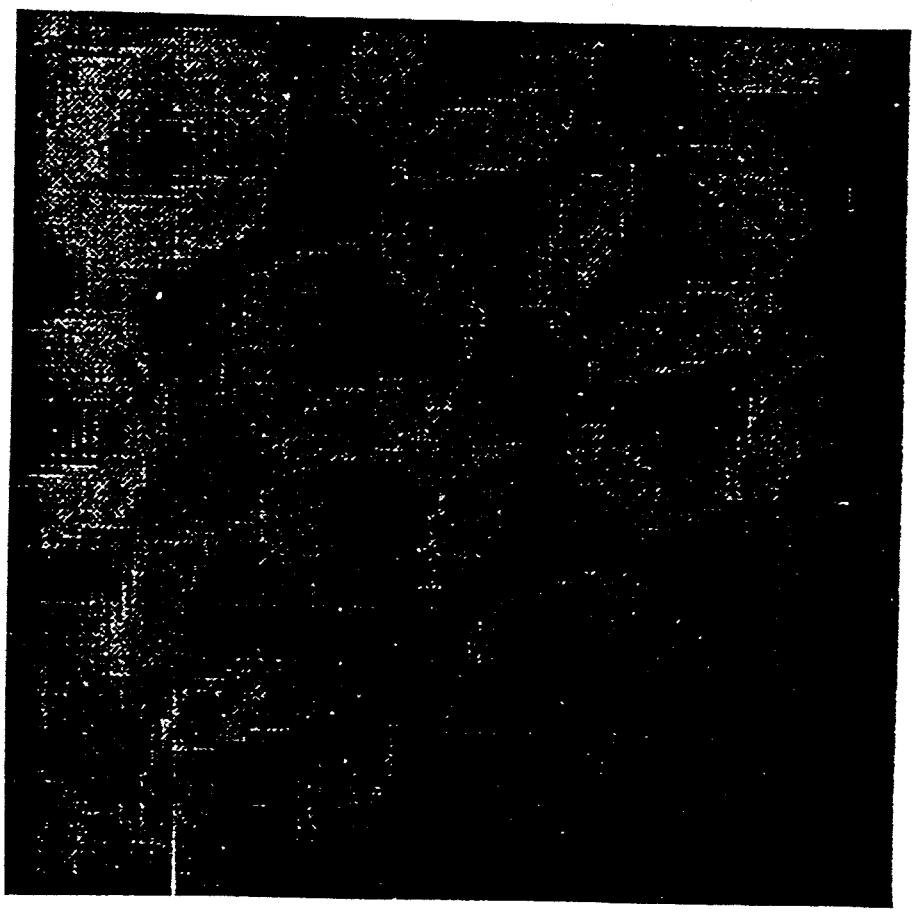
Figure 6:
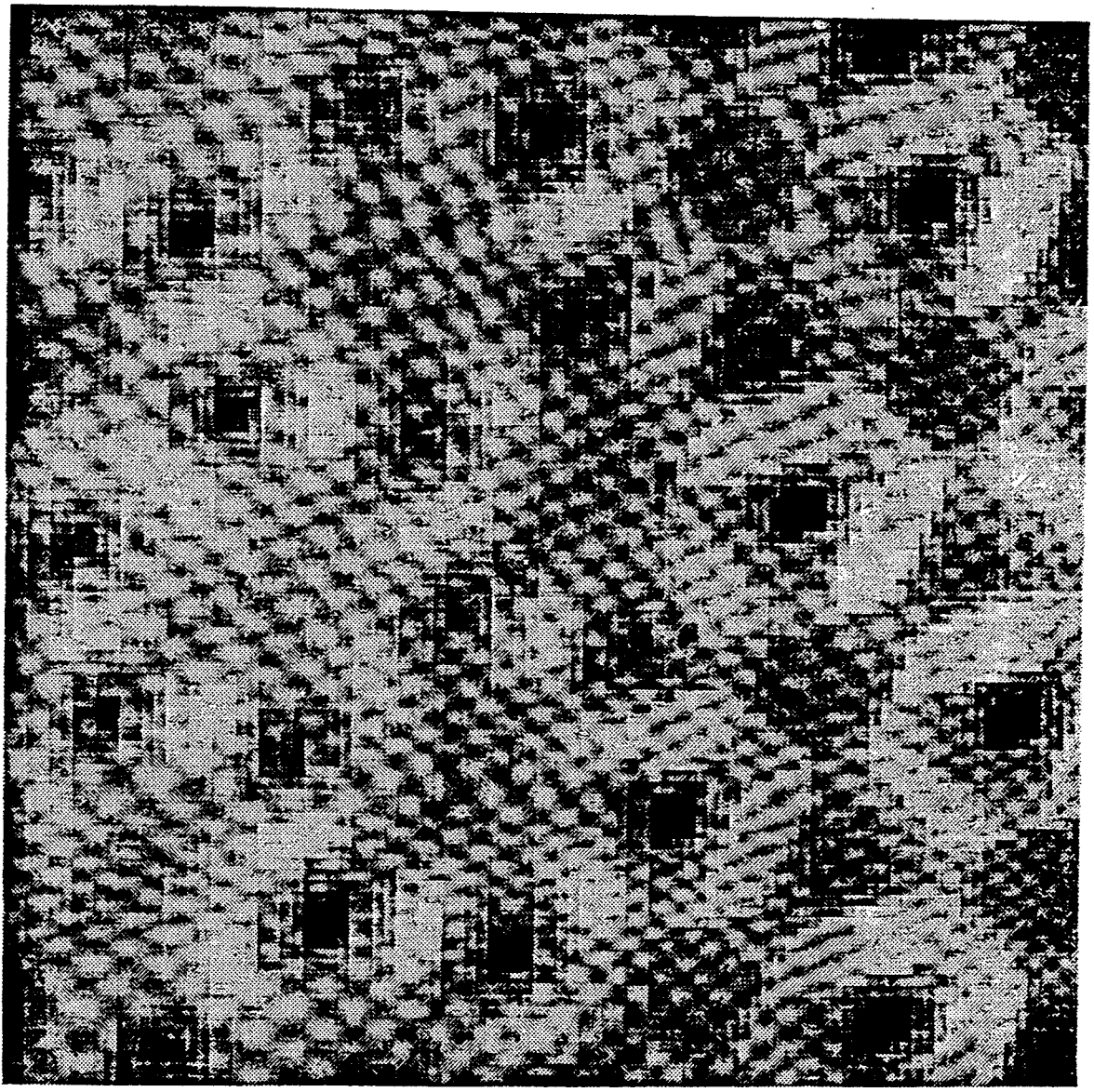

FIG. 6 combines the views of FIGS. 5 A and B for clearer comparison.

FIG. 7 sets out three equations used in the calculation of the behavior of block copolymers.

DETAILED DESCRIPTION OF INVENTION

A bicontinuous morphology is distinguished by two interpenetrating, labyrinthine networks of ordinarily immiscible substances [Scriven 1976], in which macroscopic phase separation is prevented by one of at least two possible means: 1) chemical linking between the two components, as in block copolymers; or 2) addition of surfactant. A triply-periodic bicontinuous morphology (TPBM hereafter) is further distinguished by long-range three-dimensional periodic ordering conforming to a space group. TPBMs were proposed in the late 1960's and 1970's as possible microstructures in binary surfactant/water 'cubic phases' [Luzzati et al. 1968; Lindblom et al. 1979], and in ternary surfactant/water/oil cubic phases [Scriven 1976] (cubic phases are also known as 'viscous isotropic phase' liquid crystals). This has been fairly well established for certain binary cubic phases [Longely and McIntosh 1983; Rilfors et al. 1986], but until this diclosure, demonstrated with less certainty in the case of ternary cubic phases [Anderson 1986; Fontell et al. 1986; Rilfors et al. 1986]. TPBM's have also been demonstrated in phases of cubic symmetry occuring in block copolymers [Alward et al. 1986; Hasegawa et al. 1986]. Described herein is the first polymeric microporous membrane with a highly-branched, triply-periodic network of submicron pores, which has been produced by radical chain polymerization of the oleic component (e.g. methyl methacrylate) of a ternary surfactant/water/polymerizable oil cubic phase.

"Binary" and "Ternary"

In this description, it should be noted that when the terms "binary system" or "ternary system" are used, they are not meant to exclude systems in which additional components are present but do not affect the development of the desired phase-segregation. For example, components may be present in such small relative quantities that the system is equivalent to a binary or ternary system for the purposes of this invention. Furthermore, one component may consist of sub-components which present nearly identical phase characteristics or which together present a single phase characterisic without departing from this invention. Thus, for example the definition includes a ternary hydrophobe/water/surfactant system whose water portion is a 50-50 mix of water and deuterated water and/or whose hydrophobic component is a mix of sub-components which segregate substantially together under the fabrication conditions to be applied.

The procedure used to produce the first example began with a mixture of 1 gm of the surfactant didodecyldimethylammonium bromide (DDDAB; the registry number of DDDAB is 3282-73-3), 1.4 ml of distilled water, and 0.26 ml of methyl methacrylate (MMA) which had been purified by vacuum distillation and to which had been added 0.004 gm/ml of azobisisobutyronitrile (AIBN). The mixture was stirred vigorously with a magnetic stir bar in a capped vial (when styrene was used instead of MMA, stirring had to be very gentle). After a few minutes magnetic stirring became impossible because of high viscosity, which together with optical isotropy as checked by observation between crossed polarizing lenses indicate a cubic or 'viscous isotropic' phase. At approximately the same volume fractions but with alkanes such as decane or dodecane, cubic phases have been reported by Fontell et al. [1986] and by the present author [Anderson 1986], verified in both cases by Small Angle X-ray Scattering. After equilibrating for a week at 23° C., the mixture was smeared onto the end of the plunger of a large syringe, and pushed through an 18 gauge needle into a 1.5 mm i. d. X-ray capillary. After loading and sealing of the capillary, the sample remained clear and optically isotropic. The optical isotropy of cubic phases is due to the equivalence of the three principle directions; other liquid crystalline phases are birefringent.

The capillary was then placed in a photochemical reactor having four UV lights, emitting radiation at 350 nm. The sample was exposed for 36 hours, to bring about radical chain polymerization of the MMA via the decomposition of AIBN into initiating radicals. By the end of this time the sample was opaque white in appearance.

Figure 1:
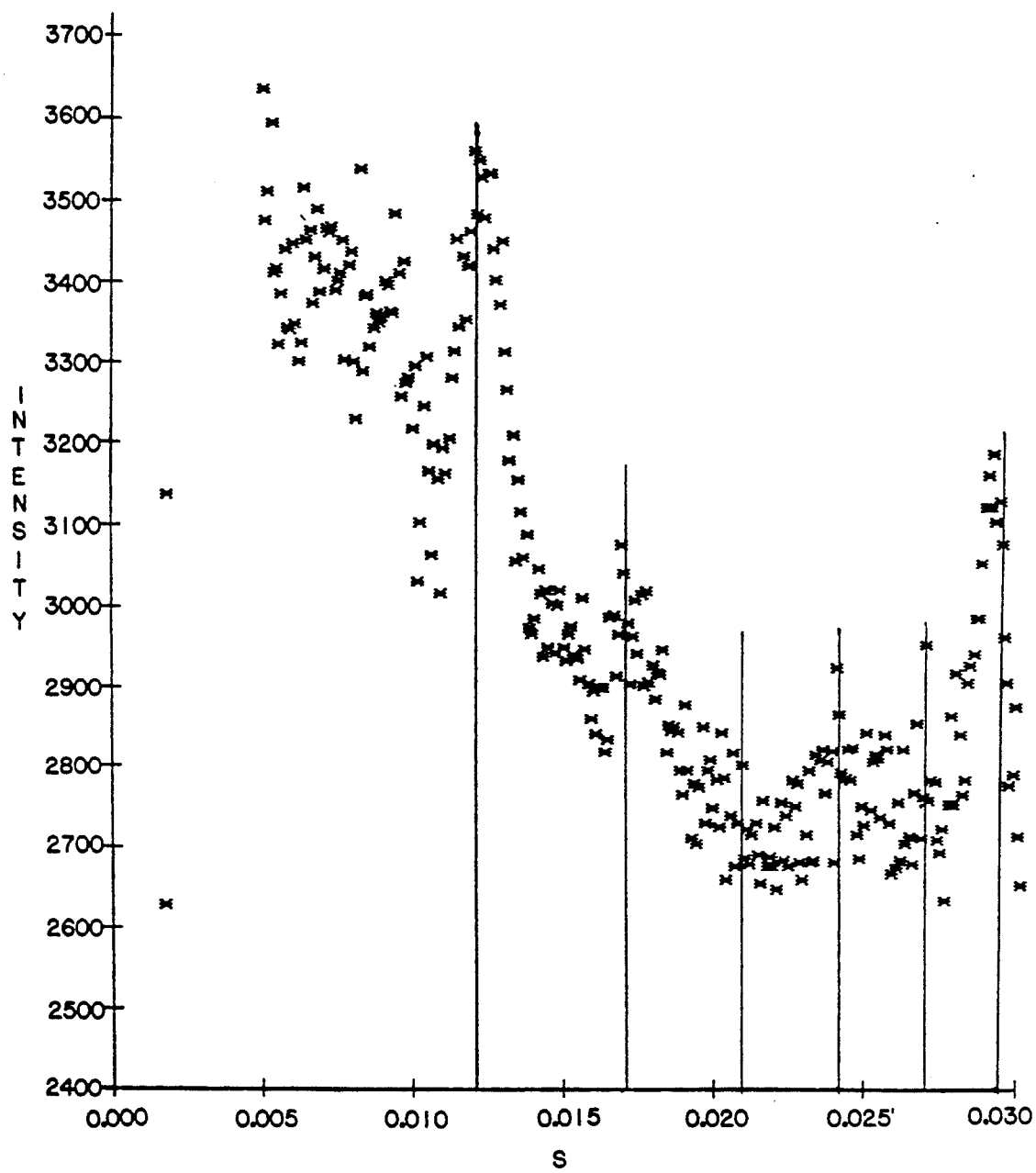
FIG. 1 shows small-angle x-ray scattering data from membrane material according to the present invention. Individual marks represent recorded intensities at each channel. Vertical lines indicate theoretical peak positions for a structure of space group Im3m and lattice parameter 11.8 nm. The label on the abscissa is $s=2 \sin(\theta)/\lambda$, where theta is one-half the scattering angle and lamda is the wave length of the radiation used. The large peak at $s=0.0025$/Angstrom is due to the main beam, and is not a reflection.

The sample was first examined by Small Angle X-ray Scattering. A Kratky small-angle camera equipped with a position-sensitive detector was used, with tube power set at 1000 watts, and data collected for five hours. The result is shown in FIG. 1, and it is clear that distinct Bragg peaks are recorded. This verifies that the sample has long-ranged periodic ordering. In FIG. 1 are indicated the theoretical peak positions for a body-centered cubic space group, Im3m, and it is seen that the theoretical peaks are represented by the data.

Recent self-diffusion measurements on DDDAB/water/dodecane cubic phases at approximately the same composition [Fontell et al. 1986] indicate that the cubic phase is bicontinuous. This was also the conclusion of the present author, with decane as oil [Anderson 1986]. That this is also true of the present phase after polymerization will be shown herein. It should be mentioned that the present applicant has shown [Anderson 1986] that SDS micelles can be swollen with monomeric styrene, and with no perceptible change in diameter after polymerization.

Figure 2:
FIG. 2 shows an electron micrograph of membrane material according to the invention. Dark regions correspond to PMMA, and light regions to void. Regions of particularly good order are outlined. (Magn. 1,000,000).
Figure 3:
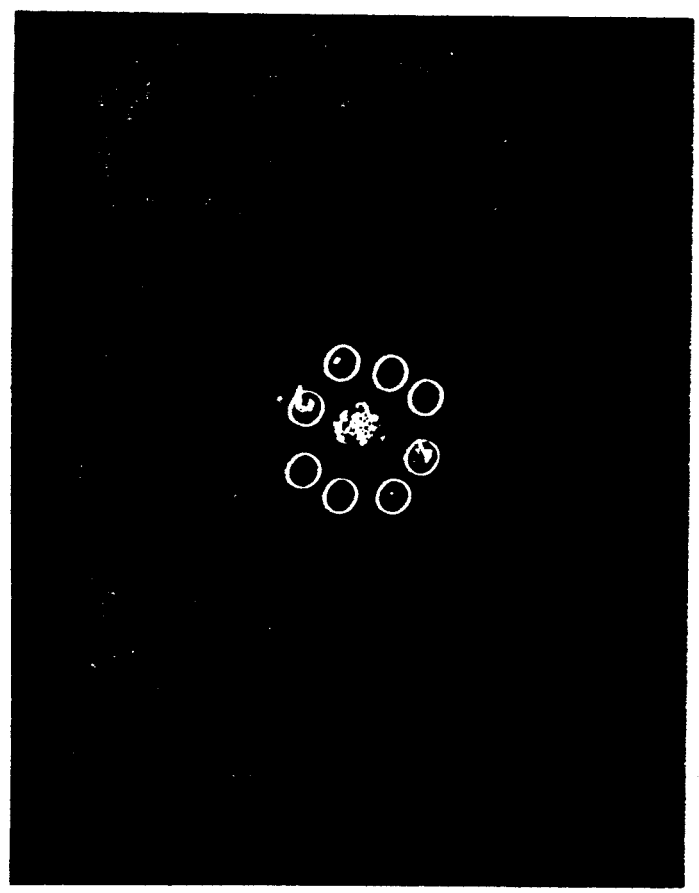
FIG. 3 is the optical diffraction pattern of the negative used to make FIG. 2. The eight-spot pattern indicated with circles provides further demonstration of cubic symmetry.
Figure 4A:
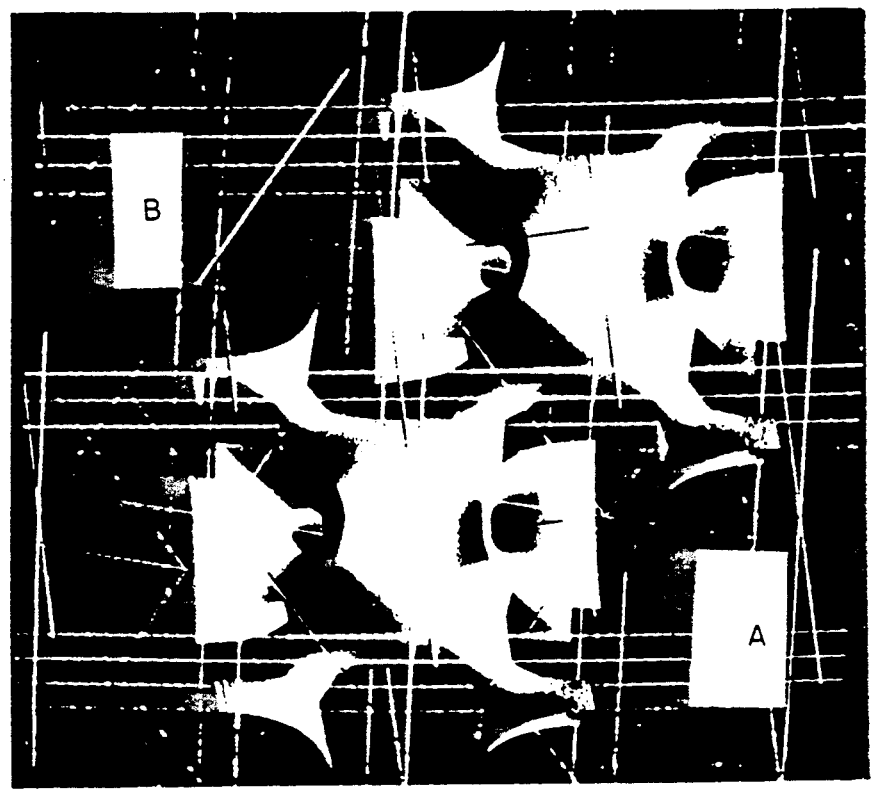
FIG. 4 A,B, and C are computer-generated pictures of a theoretical model structure, from Anderson, 1986, the applicant's doctoral thesis. The surface has constant mean curvature, and divides space into two interpenetrating labyrinths, one threaded by graph A and the other by graph B.
  A) (upper). Computer graphic, viewed approximately along the (110) direction.
  B) Projection in the (111) direction.
  C) (lower). Line drawing, without hidden line removal, from an oblique angle.
Figure 4C:
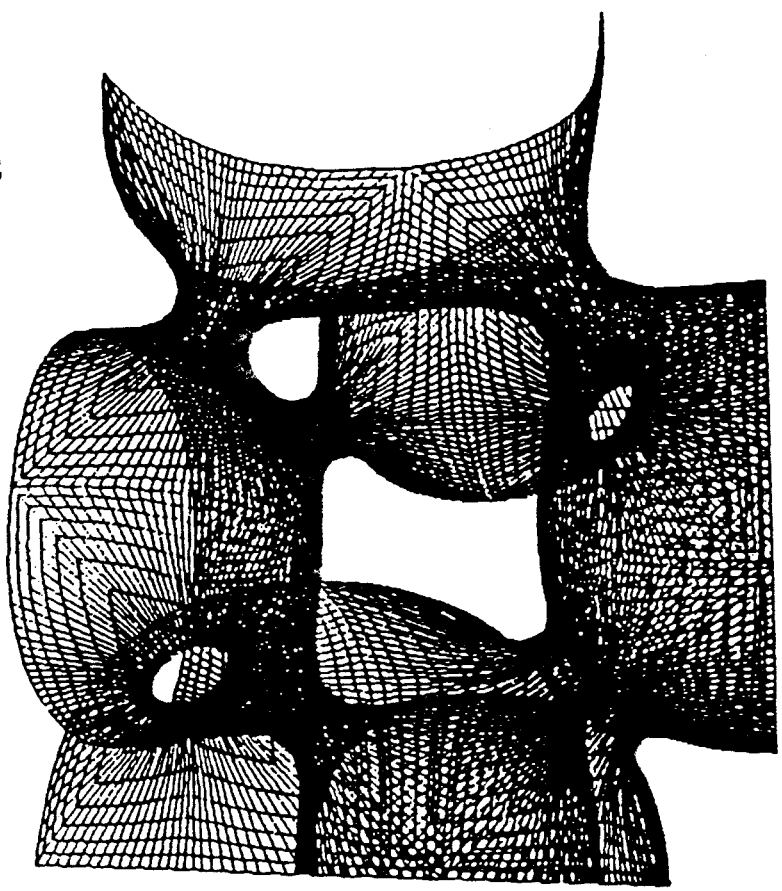
Figure 4B:
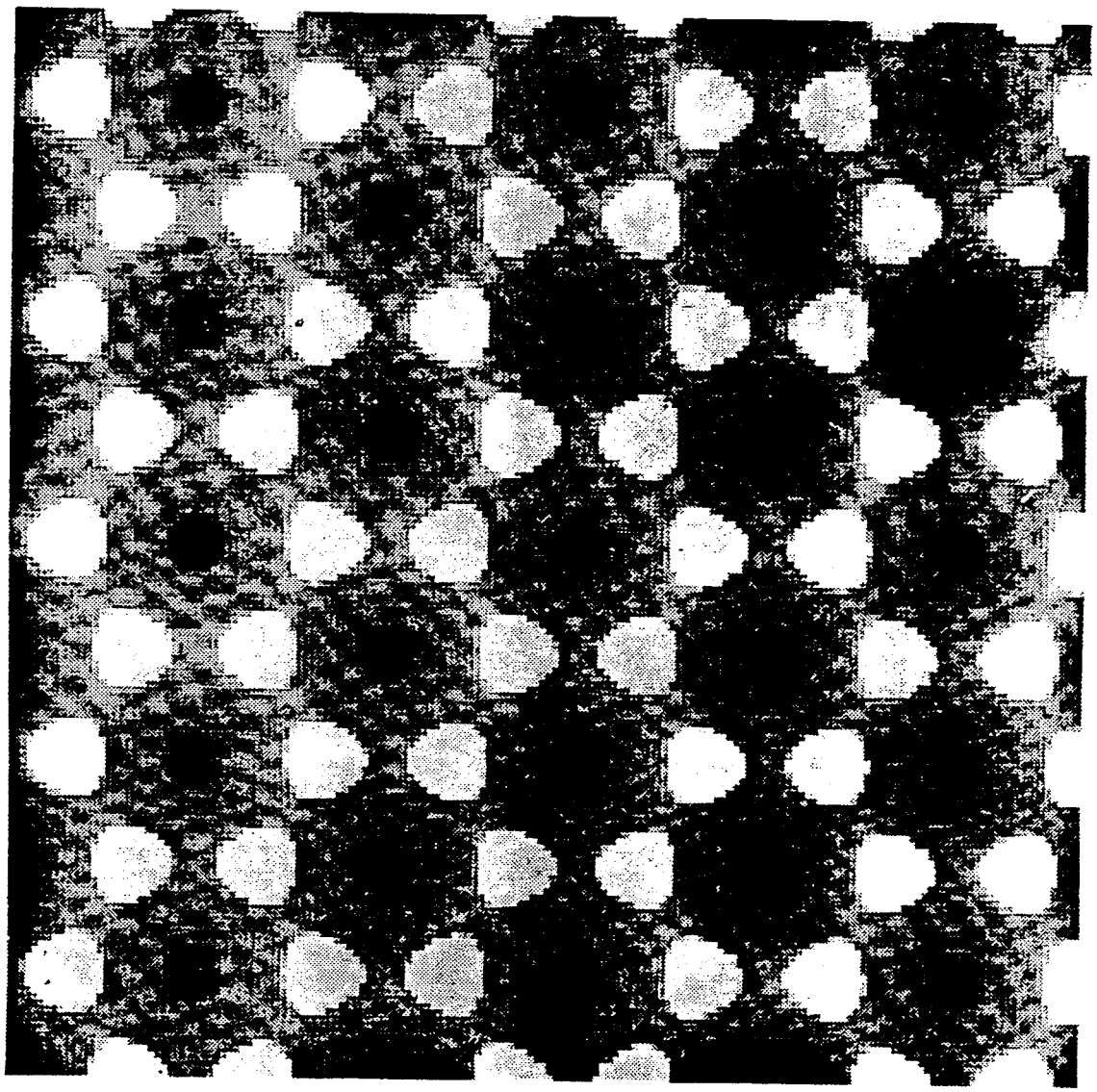

A portion of polymerized sample was dried in a vacuum oven, ultramicrotomed, and examined with an electron microscope. The forces of surface tension on drying would be expected to deform the porous PMMA structure, as would the stress induced by the microtome blade. In spite of this, the electron micrograph in FIG. 2 (magnification 1,000,000×) clearly indicates regions of periodic order, and this is substantiated by FIG. 3 which is an optical transform of the negative used to make FIG. 2. Cubic symmetry is indicated in FIG. 3 by the eight spot diffraction pattern. FIG. 4 shows a theoretical model of a TPBM of Im3m symmetry that was discovered by the present applicant [Anderson] 1986; see also Nitsche 1985]. FIG. 4a is a color computer graphic of the surface, and 4c is a line drawing of the same surface. FIG. 4b is a (111) projection of the model structure. As described in the present applicant's thesis. [Anderson 1986], the region lying on the same side of the surface as the graph A in FIG. 4a should be envisioned as being occupied by the surfactant tails and the MMA, with the region lying on the same side of the surface as the graph B containing the water and counterions, and surfactant polar groups located near the dividing surface; after polymerization, the PMMA forms a solid matrix where the MMA was located, this matrix being threaded by the graph A. The (111) projection in FIG. 4b provides a good representation of the ordered regions in FIG. 2.

The same structural model was used to explain SAXS peak positions and relative intensities for a cubic phase with decane as oil, in the present author's thesis [Anderson 1986]. Since the model represents a bicontinuous structure, it is consistent with the high self-diffusion rates measured for the same phase [Fontell et al. 1986], and with the high viscosity of the sample. This high viscosity plays an important role in preventing rearrangement of the microstructure during polymerization.

The fact that the polymerized sample can be dried and microtomed and observed under the electron beam is proof in itself that the MMA has indeed polymerized into a continuous polymeric matrix, because the microtoming was done at room temperature and MMA is a liquid at room temperature. Further proof was provided by the following experiment. The X-ray capillary was broken open and the contents put in methanol, which is a solvent for MMA but a precipitant for polymerized MMA (polymethyl methacrylate, or PMMA). In the 1.5 mm i.d. capillary, the sample was 23 mm long, so that its total volume was 40.6 cubic mm. This 23 mm section of capillary was broken up in a large volume of methanol. Since water and DDDAB are very soluble in methanol, these two components, as well as any unpolymerized MMA, were able to pass through a filter paper. However, the PMMA and the glass from the broken capillary are not soluble and did not pass through. The broken glass and the white precipitate that were stopped by the filter paper were found to have a total weight of 0.008 gm. The weight of 23 mm length of glass capillary is 0.004 gm, so that the amount of precipitate was 0.004 gm. Since the density of MMA is 1.014 gm/ml, and that of both water and DDDAB is 1.00, The mass MMA in the 40.6 cubic mm of sample investigated should have been 9.7% of that sample, which corresponds to 0.004 gm, as observed. Note that since MMA increases in density by 20% on polymerization, the volume fraction of PMMA in the capillary is only 8%. Yet the PMMA is continuous as evidenced by its integrity; a single connected piece has remained intact floating in methanol for many weeks.

The opaque white appearance of the porous polymer arises from the fact that the microcrystallite sizes are on the order of the wavelength of light, and exhibit tremendous multiple scattering due to the large refractive index difference between the matrix, which is PMMA ($n = 1.4893$ at 23° C.), and the other subspace, which is either water ($n = 1.33$) or void ($n = 1$ for vacuum, and approximately 1 for air), depending on whether or not the membrane has been dried. It is well known that cubic phases often have large microcrystallites, as evidenced by spotty x-ray patterns [e.g., Balmbra et al. 1969], and in some cases even by optical microscopy [Winsor 1974], so that 500 nm would not be unusually large.

It is, of course, possible to dry the membrane without subjecting the matrix to forces of surface tension, by a process known as critical point drying. In general this is not necessary, however, because the membrane can be kept wet at all times during use.

The membrane type described herein can be fabricated in many ways. As mentioned above, bicontinuous microstructured phases (of cubic symmetry) occur also as equilibrium morphologies in block copolymers, and chemical erosion of one component can result in a similar membrane type. It has been shown [Alward et al. 1986] that the lattice size scales as the $\frac{2}{3}$ power of the molecular weight of the copolymer, if the ratio of the two components is fixed. Since anionic polymerization reactions can produce star-block copolymers with extremely narrow molecular weight distributions, fabrication with copolymers provides a means of producing a membrane of prescribed pore size.

The surfactant DDDAB was chosen for the fabrication of this first example because it has been shown to form bicontinuous phases with many oil-like compounds: hexane through tetradecane [Blum et al. 1985]; alkenes [Ninham et al. 1984], and cyclohexane [Chen et al 1986]; brominated alkanes [present author, unpublished]; and mixtures of alkanes [Chen et al. 1986]. However, an extensive study of cubic phases [Rilfors et al. 1986] indicates that bicontinuity is the rule rather than the exception. Therefore there exists a wide variety of ternary systems that provide possible paths to the type of membrane described herein. In addition, binary water/polymerizable surfactant cubic phases could provide another route, although it is doubtful whether porosities of 90% could be obtained in this manner, since binary cubic phases generally occur near 50/50 surfactant/water. Zadsadsinski [1985] has synthesized a polymerizable phospholipid, and produced lamellar phase liquid crystals which retained the same periodic spacing after polymerization, as checked by electron microscopy [Zadsadsinski 1985] and by SAXS [present author, unpublished]. Alternatively, a similar end product can be obtained by chemical alteration of a cubic phase formed from block copolymers, as mentioned above. One aspect of the present invention relates to the final product irrespective of the particular process used to derive it. The polymerization of the oleic component of a binary or ternary hexagonal phase, or chemical alteration of a block copolymer cylindrical phase, to yield a membrane with a doubly-periodic arrangement of cylindrical pores, would also be an useful modification of the present invention, as would the polymerization of a microemulsion containing a polymerizable component (for the definition of a microemulsion, see [Danielsson and Lindman 1981]).

Other modifications of the process could produce membranes with special properties. For example, proper choice of monomer which forms an ionomer on polymerization would result in a membrane with electrically charged tunnels. Or the monomer could be chosen to form a conducting polymer on polymerization. Or if the matrix were made with opposite ion-selective properties on its two sides (as should be possible in principle with ternary cubic phases using a polymerizable surfactant, since one side of the surfactant-laden interface is polar while the other is nonpolar), then a bipolar membrane with a great deal of surface area would be obtained. In other words, in some cases two distance, interwoven but disconnected porespace labyrinths are created, each of which are continuous, highly regular, highly branched an inter-connected with itself, each having globally uniform effective pore size; the distinct porespace labyrinths being separated by a continuous stabilized dividing wall, the wall having two distinct surface, each surface facing one respective porespace labyrinths. The distinct surfaces may be given different properties. Another possible means of achieving the same end would be to form a cubic phase using a triblock copolymer. Thus, in addition to providing a range of pore sizes that overlaps with that provided by zeolites but extends to much larger sizes, the new membrane type provides the possibility of high porosity, high coordination number, triply-periodic porous media with either nonpolar or polar characteristics.

MATERIALS AND PROCESS VARIATIONS

There are many potential processes and combinations of materials that could produce polymeric membranes with triply-periodic, submicron porespaces from thermodynamically stable or metastable bicontinuous triply-periodic phases. Possible routes to the fabrication of such a membrane will now be discussed, with an eye toward different membrane applications and the membrane characteristics called for by each. These routes fall into two general classes:

1) polymerization or solidification of a component or components of a surfactant-based triply-periodic fluid phase; and
2) chemical degradation of one or more blocks in a multiblock or graft copolymer-based triply-periodic phase.

There are some important similarities between these two approaches as well as distinctions; for nonionic surfactants can be made which have as few as 20 carbons (see [Kilpatrick 1983] for a discussion of the minimum carbon number for these amphiphilic alcohols to be true surfactants), or with molecular weights of thousands when they are referred to as block copolymer polyol surfactants [Vaughn et al. 1951], and it is possible that there is a continuum of bicontinuous cubic phases with increasing surfactant-molecular weight that at low Mw yield membranes after a polymerization reaction, and at high Mw yield membranes on the removal of other component(s). Following a discussion of the two classes, methods will be discussed for fabricating triply-periodic ionomeric membranes by similar means or by modifications of neutral membranes of the type described.

Finally, a hybrid process will be dicussed in which a membrane formed by a type 1) process (or less likely a type 2) process) is infiltrated with a polymerizable material that is then polymerized, after which the original material is eroded away. In such a process the initial membrane would be of low porosity, say 10%, so that a 90% porosity membrane would finally result, and there would be a great deal of freedom in choosing the final monomer since the triple-periodicity would already be imposed by the initial membrane. A further variation of this process would be to infiltrate with a polymer that is above its melting temperature, and then allowing the polymer to solidify; the polymer that formed the original matrix would then be dissolved away by a method such as those discussed in this section.

Class 1) Processes

In the first general class of procedures, a surfactant or mixture of surfactants is needed, which may or may not be polymerizable, and except in the case of a binary polymerizable surfactant/water mixture, another nonaqueous, usually oil-like or at least hydrophobic component which must be polymerizable if the surfactant is not. Since the working definition of a surfactant is an amphiphile which is capable of cooperativity such as that needed to form a liquid crystal, any amphiphilic compound or mixture of compounds that can form a triply-periodic fluid phase together with water and/or another nonaqueous component would have to be considered a surfactant, whether or not that title or some other title such as cosurfactant, amphiphile, block copolymer or alcohol were traditionally used for the compound or mixture (recall that cubic phases are considered 'liquid crystals' by convention). For example, recent work in Sweden [Guering and Lindman 1983] has shown that bicontinuous microemulsions can be formed with alcohols that are normally used as cosurfactants. Also, work in that same group [Lindman 1986] has shown that bicontinuous phases can be formed without water, using water substitutes; because the same is probably then true of bicontinuous cubic phases, and because it should be possible to form bicontinuous cubic phases without any water-like component such as with a binary surfactant/oil mixture, water should not be considered essential to the process although it will nearly always be involved (it is interesting that there has been nearly as much work done on surfactant/oil/-pseudo-water microemulsions as on binary surfactant-/oil liquid crystals, largely because of the long equilibration times necessary in the latter case).

Another possible variation of process type 1) would be to form a bicontinuous triply-periodic phase with a surfactant, water, and a polymer above its melting point. Once the phase has been annealed it would be brought down below its melting temperature and the solidified polymer would then exhibit triply-periodic porosity. Such a variation of the process would allow a much larger variety of polymers since they could be synthesized beforehand under any desired conditions. The applicant has done work [Anderson (2)] in which a calculation of the thermodynamics of bicontinuous cubic liquid crystal morphology is compared with that of the competing morphologies—lamellar, normal and inverted hexagonal, and normal and inverted discrete cubic phases—to predict phase behavior based on certain molecular parameters. The dominant geometry-dependent energies are the so-called curvature energy, which results from the packing of the surfactant molecules at the hydrophilic/hydrophobic interface, and the entropic energy of stretching or compression of the surfactant tails, the two energies also considered dominant in a qualitative discussion by Charvolin [1985]. The publication will indicate that the bicontinuous cubic phase structure should be expected for a wide variety of systems, because such structures can satisfy curvature requirements while simultaneously keeping stretching energies small. For example, for the family of constant-mean-curvature surfaces (which minimize area under the constraint of a given volume fraction) with the double-diamond symmetry (space group Pn3m) [see Anderson 1986], the author has shown that the standard deviation in the distances which the surfactant molecules must reach is only 7% of the average distance. Furthermore, it is known that addition of oils to surfactant/water mixtures can change phase behavior by relieving stretching energy costs Kirk and Gruner 1985], so that bicontinuous cubic phases should be expected to arise on the addition of a third component, as in the case of DDDAB/water.

As mentioned elsewhere in this disclosure, polymerizable surfactants have been synthesized [Zadsadsinski 1985], and liposomes made with the surfactant in water showed no change in structure on polymerization, as measured by both x-ray diffraction and electron microscopy. The particular surfactant synthesized was a double-tailed phospholipid, with each tail containing one polymerizable double bond. Recently a great deal of interest has arisen in the chemical and biological sciences in the idea of using polymerizable surfactants to study surfactant microstructures. As more types of polymerizable surfactants become available and more is learned about using them, the choices of materials available for fabricating a membrane of the type described herein from binary polymerizable surfactant/water triply-periodic phase will continue to broaden. It is now firmly established that phospholipids form bicontinuous cubic phases [Longeley and McIntosh 1983; Lindblom et al. 1979; Hyde et al. 1984; for a review see Rilfors et al. 1986]. A membrane formed by polymerizing such a cubic phase would be zwitterionic.

Bicontinuous cubic phases have also been formed with a variety of ionic surfactants. In fact the first proposed bicontinuous cubic phase was in a binary soap system, potassium laurate/water [Luzzati and Spegt 1967]. Other examples of binary bicontinuous cubic phases formed with anionic surfactants are: sodium laurate, and relatives with other chain lengths [Luzzati et al. 1968]; potassium octanoate, and with other chain lengths; and sodium ethylhexyl sulfosuccinate (Aerosol TO)/water [Linblom et al. 1979]. An example of a binary bicontinous cubic phases with cationic surfactants is dodecyltrimethyl ammonium chloride/water [Bull and Lindman 1974]. It has also been long known that many soaps, such as the strontium and cadmium soaps, form single-component cubic phases in which the hydrocarbon and ionic regions are each continuous [Luzzati and Spegt, 1967; also Luzzati et al. 1968]. Calcium p-ethyl-w-undecanoate forms such a structure at room temperature [Spegt 1964]. Such a structure is to be considered bicontinuous in that the hydrocarbon and ionic groups in the anhydrous crystal are normally dispersed in such a way that either the polar groups or the hydrocarbon tails are segregated into discrete domains. Chemical attack on one of these moieties could yield a triply- periodic microporous solid, with either polar or nonpolar channels depending on the nature of the chemical erosion.

While all of the well-established bicontinuous triply-periodic phases are in fact of cubic crystallographic symmetry (in equilibrium; viz., in the absence of stress forces), there is no reason to believe that triply-periodic structures of other symmetries such as tetragonal, hexagonal, orthorhombic or other could not be found. Although it has not been demonstrated with scientific rigor, a bicontinuous phase of tetragonal symmetry, space group I422, was proposed by Luzzati et al. [1968]. In fact, triply-periodic minimal surfaces, of the type invoked in the modern treatment of bicontinuous liquid crystals, having three-dimensional noncubic space groups are discussed by Schoen [1970], and in the applicant's thesis [Anderson 1986]. The 'R' phase proposed by Luzzati et al. has not been substantiated but if such a structure did exist it would be well represented by the triply-periodic minimal surface of hexagonal symmetry discovered by Schwarz [1890] and called H'-T by Schoen [1970], or by a surface of constant, nonzero mean curvature of the same space group and topological type [see Anderson 1986]. Other models of bicontinuous structures, satisfying the very strong constraint of a constant-mean-curvature interface (the area-minimizing configuration), which are triply-periodic but have noncubic space groups, are presented in the author's thesis.

It should not be surprising that binary surfactant/water cubic phases have shown the ability to solubilize various hydrophobic or amphiphilic components. The cubic phase in the 1-monoolein/water binary system has been shown to solubilize diglycerides [Larsson 1967], protein, and cholesterol up to a molar ratio of 1:3 with monoolein. Interestingly, a bicontinuous cubic phase in the dioleoylphosphatidyl glycerol/water system can actually solubilize the anesthetic dibucaine [Rilfors et al. 1986]. DDDAB and water can solubilize up to 11% dodecane in a bicontinuous cubic phase, and also styrene and methyl methacrylate as shown herein, as well as other alkanes [Fontell 1986]. The soap sodium caprylate with water forms cubic phases with a variety of organics solvents including heptane, decane, and p-xylene [Balmbra et al. 1969]. A bicontinuous cubic phase has been found in the ternary sodium octanoate/octane/water system [Rilfors et al. 1986]. Thus there are substantiated examples of ternary bicontinuous cubic phases with zwitterionic, cationic, and anionic surfactants.

Bicontinuous phases also occur in ternary phase diagrams as islands which do not contact the binary surfactant/water edge—that is, they cannot be obtained by addition of a third (usually oleic) component to a binary cubic phase. This is easy to understand, in that removal of the third component forces the surfactant tails to reach to regions far from the hydrophilic/hydrophobic dividing surface, regions that could otherwise be filled by the third component [Kirk and Gruner 1985]. Thus no cubic phase occurs in the DDDAB/water binary system, even though the addition of only a few percent oil can yield a bicontinuous cubic phase.

It is quite possible that very inexpensive yet effective surfactants, produced from vegetable oils, will soon become available. Acylated ester sorbitol surfactants have recently been made using lipase enzymes in organic solvents such as pyridine [Klibanov 1987], and surface tension and emulsification experiments showed a high degree of surfactant behavior, higher in fact than analogous synthetic surfactants. In view of the surplus of carbohydrates in the United States, this method may prove to be a very economical source of surfactants in the near future. Since interfacial tensions as low as 0.1 dynes/cm have been measured between hexane and water using such a surfactant, it is likely that fluid microstructures, such as microemulsions, are forming in a narrow interfacial region. It is now generally agreed that bicontinuous microemulsions are responsible for the lowest oil/water interfacial tensions, so that these surfactants appear to have a sufficiently well-balanced HLB to form bicontinuous phases, including perhaps bicontinuous cubic phases.

Block copolymer polyol surfactants were first manufactured under the trade name PLURONIC by BASF Wyandotte Corporation in 1950. Among the epoxides used as the hydrophobic blocks are [U.S. Pat. No. 3,101,374]: propylene oxide, butadiene monoxide, 1,2-butylene oxide, styrene oxide, epichlorohydrin, cyclohexene oxide, tetrahydrofuran, and glycidyl alkyl ethers; these epoxides satisfy the condition that the oxygen to carbon ratio is not greater than 0.4. And among the epoxides used as the hydrophilic blocks are: ethylene oxide, glycidol, butadiene dioxide, all of which have a oxygen to carbon atom ratio at least 0.4. The molecular weight of these surfactants can be as low as 767 ('PE 71') or can be in the thousands. As mentioned above, the ethoxylated alcohol C12E8 is of low molecular weight but is a true surfactant [Kilpatrick 1983]. Therefore there is a variety of chemical units, and a wide range of molecular weights that can yield these types of surfactants, and there exist at least three means by which such a surfactant could be used to obtain a membrane of the present type: a) a cubic phase could be formed with a polymerizable third component (or second component if water is unnecessary) and this component polymerized; b) the surfactant itself could be made polymerizable; or c) if the molecular weight of the block copolymer surfactant were high enough, the copolymer could provide the membrane matrix, after removal of one of the blocks by chemical erosion or of one or more additional components such as the water and or a third component, which might not call for any chemical erosion. The key point about the tremendous range of molecular weights over which the polyol surfactants are available is that the pore size of the resulting membrane can be controlled over a very large range, possibly into the range of thousands of Angstroms.

In the third part of this section, possible methods are discussed for converting a neutral membrane of the present type into an ion-exchange membrane, but another possible means to achieve the same end would be to choose a monomer that on polymerization would yield the desired ion-exchange characteristics. Polymethacrylic acid and polyacrylic acid are weak-acid cation-exchange polymers, for example, and since methyl methacrylate (which is quite polar) is easily incorporated into the DDDAB/water cubic phase, it is possible that the same process could yield an ion-exchange membrane.

Plasma is another means by which polymerizations could be carried out in cubic phases, and it is known that hydrophobic monomers such as 4-picoline and 4-ethylpyridine can become hydrophilic polymers on plasma polymerization.

Photoinitiation by, for example, ultraviolet light is a very inexpensive means to polymerize a monomer, and also versatile, so that if volatile components were needed the mixtures could be protected from evaporation losses by materials transparent to UV light—such as quartz if thick walls were necessary (which is unlikely since photoinitiation is usually done at atmospheric pressure) or ordinary glass if thicknesses are not large and the UV wavelength is kept at or above 350 nm.

In the actual production of membranes, polymerization by photoinitiation will be much simpler and quicker than in the main example detailed in this disclosure because thicknesses will be on the order of microns rather than millimeters.

It is important to stress that the surfactant should be recoverable from the membrane in a simple post-polymerization step for recycling, using a solvent for the surfactant which is a not a good solvent for the polymer as was done with methanol in the main example. Since the UV light need only penetrate micron-thick layers and since the photoinitiator can be chosen to be much more sensitive to UV light than the surfactant, and since the reaction can be done at room temperature and pressure, the polymerization reaction should have little effect on the surfactant. Another important characteristic of this general process type is that, because cubic phases are equilibrium phases and are extremely viscous, transient conditions that might affect other fluid microstructures (such as low viscosity, temperature-sensitive microemulsions) have much less effect—as evidenced by the retention of cubic lattice ordering after polymerization in the main example—making the fabrication process flexible and reliable. Thus there is no reason why class 1) processes should be limited to polymerization by photoinitiation; initiation could be by thermal decomposition, redox, radiations such as neutrons, alpha particles or electrons, plasma as mentioned above, or even electrolysis [Pistoia and Bagnerelli 1979]. It is even feasible for a condensation polymerization to be performed, if the condensate is something like water or a short-chained alcohol that would be incorporated into the water phase or the surfactant-rich interface. From the standpoint of the stability of the finished membrane, it should be remembered that addition polymers generally have greater thermal and chemical stability than condensation polymers.

Particularly in view of the variety of surfactants capable of forming bicontinuous cubic phases, there is a wide range of monomers that have potential for the basis of the matrix material in process type 1). Two monomers that have proven particularly successful are styrene and methyl methacrylate. Thus polar (PMMA) and nonpolar (PS) membranes have been produced. Both PMMA and PS are very inexpensive, about $0.30-$0.60 per pound. As discussed elsewhere, the same surfactant DDDAB forms bicontinuous phases also with alkanes, cyclohexane, brominated alkanes, mixtures of alkanes and, significantly, alkenes. The latter is significant because the presence of carbon double-bonds makes these polymerizable, such as with a Ziegler-Natta catalyst; note that such a polymerization would yield a stereospecific polymer. Isotactic and syndiotactic PMMA can be prepared with Ziegler-Natta catalysts, and these have been used in dialysis membranes [Sakai et al. 1980]. Isotactic polystyrene has high thermal and hydrolytic stability as well as stiffness. Other relatives of PMMA provide potential materials for process 1) membranes, some offering particular advantages for certain membrane applications. As mentioned above, methacrylic acid is a relative of MMA that is the basis of some weak-acid cation exchange membranes, as is acrylic acid. Often copolymers with divinyl benzene are used. Another member of the acrylic family, polyacrylonitrile, is commonly used in UF membranes (usually as a copolymer with a few mole percent of another monomer such as styrene or vinyl chloride), and these are resistant to both hydrolysis and oxidation.

Polyvinyl chloride (PVC) and its copolymers (such as with vinyl acetate) are free-radical initiation polymers which are also important membrane materials. PVC exhibits high stiffness and good solvent resistance, and is inexpensive. Chlorinated PVC is denser and exhibits greater thermal stability. Copolymerization with propylene yields a polymer that is resistant to most acids, alkalis, alcohols, and aliphatic hydrocarbons.

Later in this section we discuss other classes of monomers that can be used in type 1 processes.

The variation of the process described above in which a polymer above its melt temperature—or at least at high enough temperature to allow sufficient mobility for a triply-periodic phase to form—is incorporated into a surfactant-based phase, and the polymer then solidified into a membrane matrix, could be used to form a triply-periodic membrane with other polymeric materials that are particularly well suited for certain membrane applications. Among these are:

polyethylenes (as in Celgard membranes), and its copolymers such as with vinyl acetate or acrylic acid, or with propylene as in polyallomers;

fluorinated polymers, such as polytetrafluoroethylene, polyvinylidene fluoride, polyfluoroethylene-propylene, polyperfluoroalkoxy, and polyethylene-chlorotrifluoroethylene. Membranes made from perfluorinated ionomeric polymers are now more important than all other ionomeric membranes combined;

polyorganosiloxanes (silicones);

cellulose and its derivatives, including cellulose nitrate, cellulose acetate and triacetate (in a binary surfactant/polymer cubic phase, since cellulose is extremely hydrophilic):

polyamides, which fall into three subclasses, fully aliphatic, aromatic, and fully aromatic, all three of which have examples that are used as membrane materials. Membranes made from polypiperazines exhibit long lifetimes and chlorine resistance;

other special polymers, such as polyparaphenylene sulfide which is melt-processable and can readily be made conducting [Baughman et al. 1983]. Such processes are now more feasible in light of new research [Charvolin 1985] on naturally-occuring surfactants with very good thermal stability. Alternatively, the polymers could be solidified inside the pore space of a triply-periodic (low porosity) membrane made of dissolvable material, avoiding the necessity to subject the surfactant to elevated temperatures.

Class 2) Processes

In this class of procedures, a triply-periodic phase is prepared which incorporates a multiblock or graft copolymer, using a solvent or temperature elevation, or both, to enhance mobility, and one or more of the blocks form(s) the membrane matrix after elimination of one or more component(s) to form the pore space. In general this appears to be a more difficult process than type 1) processes because of the following reasons:

a) expensive anionic polymerizations have been necessary thus far to produce copolymers sufficiently monodisperse to form triply-periodic phases;

b) because of the inherently lower mobility of copolymers relative to small-molecule surfactants, more involved annealing procedures employing solvents and elevated temperatures are generally needed;

c) dissolving away one labyrinth of solidified polymer while leaving another labyrinth intact is generally difficult; and d) porosities higher than 70% will be extremely difficult to obtain, and higher than even 40% will be difficult, with this process.

On the other hand, in this method, as in some of the variations of type 1) processes discussed above, the polymerization reaction(s) can be carried out before the formation of the triply-periodic phase. The study of the morphologies of phase-segregated block copolymers is quite young and has not received a great deal of attention. Therefore very little is known about the occurance of bicontinuous cubic phases in block copolymers. Generally speaking, however, the situation is in many ways simpler than in surfactant systems where electrostatic interactions between surfactant head groups play a dominant role in determining microstructure. In diblock copolymers, on the other hand, the morphology is essentially determined by the immiscibility of the two covalently bonded blocks, so that two diblock copolymers, with the same volume ratio between the two blocks, should to first order be expected to exhibit the same morphology. To a large extent this has been borne out by the diblock and star-block copolymers whose phase behavior has been studied; at nearly 50:50 volume fraction ratios between the two blocks, lamellae generally are present; at high volume fraction ratios, approximately 80:20 or higher, spheres are present; and in between one finds cylindrical morphologies or bicontinuous cubic morphologies, the latter generally restricted to a narrow range near 30:70. This is also the situation predicted by simple [Inoue et al. 1968] and more sophisticated theories Leibler 1980: Ohta and Kawasaki 1986], except that these theories were developed before the discovery of bicontinuous block copolymer morphologies and so did not include these possibilities. Thus, the proof of the existence of bicontinuous cubic phases in star-block [Thomas et al. 1986] and in linear diblock [Hasegawa 1987] copolymers indicates that these phases will be found in a variety of copolymers as studies of morphology continue, now that the identity of the phase has been established.

Further indication that bicontinuous cubic phases should be found in many block copolymers near 70:30 volume fraction ratio lies in the fact that the 'double diamond' bicontinuous cubic morphology has been found at both: i) 30% polystyrene outer blocks, 70% polyisoprene inner blocks in 6-18 arm star-block copolymers; and ii) 30% polyisoprene outer blocks, 70% polystyrene inner blocks (i.e., interchange PS and PI); as well as in iii) 34% polystyrene, 66% polydiene linear diblock copolymers. It is in fact the case that in the third example, the discoverer (Hashimoto) had many years ago taken SAXS and electron microscopy data on the phase and not understood the data, until hearing of the work by Thomas et al. Thus it is likely that triply-periodic morphologies occur in many block copolymers, although it appears that they are generally confined to narrow volume fraction ranges near 70:30. It also appears that the polydispersity of the copolymer cannot be too high: the studies on bicontinuous cubic phases in copolymers have thus far used only highly monodisperse copolymers (polydispersity indices less than 1.05) prepared by anionic polymerizations, and it is quite possible that such well-ordered morphologies are the result of well-ordered materials!

The preparation of block copolymer TPBMs with polystyrene/polyisoprene is described in [Alward et al.1986] and [Thomas et al. 1986]. The choice of solvent and annealing temperature will of course depend on the polymers used, but the general procedure will be similar. What was not carried out, however, was the leaching out of one phase to create voidspace. Methods and materials will now be discussed for such a process.

If one of the blocks, call it block A, contains double bonds in the backbone, such as the rubbers polyisoprene and polybutadiene, and the other block(s) do(es) not, then ozonolysis can provide a means to leach block A. Following treatment with ozone to form ozonides, the decomposition of the ozonides can be accomplished in a number of possible ways: 1) they can be oxidized, for example using a reduced platinum oxide catalyst; 2) they can be decomposed by steam distillation, using an alcohol solvent, in which case no reduction step is necessary; 3) a modification of 2) is to carry out the ozonolysis in an alcohol such as methanol; 4) reducing agents such as zinc dust in acetic acid can be used.

If the block A is chosen to be radiation sensitive, with the other block(s) insensitive, then in view of the small thicknesses of membranes it should be feasible to destroy block A with radiation and leave a relatively intact polymer matrix. Many polymers suffer degradation on intense radiation, and in fact some are used in the electronics industry, for example, as negative photoresists due to this property. PMMA is radiation sensitive, for example, and PMMA/polyisoprene or polybutadiene copolymers should be capable of forming bicontinuous cubic phases, in analogy with polystyrene.

As in nucleation-track membranes, a combination of ionizing radiation and chemical etching could be used that would be selective to one block. It is known that for every polymer (in fact every substance) there is a lower limit of heavy ion mass below which tracks are not produced. For example, tracks are produced in cellulose nitrate by hydrogen ions, while Mylar (polyethylene terephthalate) requires ions at least as heavy as oxygen. A diblock copolymer selectively tracked in one component could then be immersed in acid or base to etch away pores. Olefin metathesis is another reaction that is used today to degrade polymers. Again what is required is the presence of double bonds in the polymer backbone, so that as in the discussion of ozonolysis the PS/PI block copolymers would be archetypical candidates. In general such reactions require more critical conditions than ozonolysis, and also ozone being a very low MW gas means that penetration through the porespace would be more easily accomplished with ozone. Attack of one block by other chemical means such as with acids is of course possible. For example, polyesters and polyethers can be cleaved under acidic conditions.

Thermal decomposition, by choosing one block with a lower ceiling temperature, is another possible means, which could circumvent the need for reactive chemicals. For example, poly-a-methyl styrene undergoes an unzipping reaction above 50 degrees C.

Biodegradable polymers are another possibility, currently of interest because of their application in controlled drug-release. Homopolymers and copolymers of lactic, acid and glycolic acid are examples that have been examined for use in the body, but many other biodegradable polymers have been investigated for applications to the dispensing of herbicides and insecticides.

In the last part of this section, possible methods are discussed for modifying neutral polymers to form ionogenic polymers, but of course another possible means to produce an ionomeric membrane is to use a type 2) process in which the block(s) that will determine the membrane matrix is (are) ionogenic. Ionomeric membrane polymers that could be copolymerized with a leachable polymer include random copolymers with etylenically unsaturated monomers containing ionogenic groups. The first such example was a copolymer of acrylic acid with ethylene incorporating inorganic ions [Surlyn]. Other examples include ethylenically unsaturated monomers containing sulfonate groups copolymerized with acrylonitrile, and monomers containing quaternary ammonium or weakly basic groups. Ionomeric step reaction polymers include polyurethanes with quaternary ammonium groups in the backbone, in which case these ionomers are also called ionene polymers. Among other ionomeric materials that could form blocks in a block copolymer are those modifications of neutral polymers discussed in the last part of this section. Generally speaking, the chemistry of block copolymerizations and linking reactions has seen considerable growth in recent years, and in the future the availability of block copolymers with desired block properties will increase.

In order to understand and predict the occurrence of triply-periodic bicontinuous morphologies in block copolymers, the applicant has developed a statistical mechanical theory that compares the free energies of the known morphologies in the strong-segregation limit. The theory combines the results of Ohta and Kawasaki [1986] and de la Cruz and Sanchez [1986], and is an improvement over the approach of Ohta and Kawasaki in that the exact expression for the static structure factor of a star diblock copolymer (equation 28 in de la Cruz and Sanchez), which includes the linear diblocks treated by Ohta and Kawasaki as a special case (n=1), is used in the computation rather than an approximation (as in equation 3.19 of Ohta and Kawasaki). Furthermore, and of prime interest here, the triply-periodic bicontinuous morphology named the 'ordered bicontinuous double-diamond' in Thomas et al. [1986] has been evaluated in the free energy comparison. The calculation will now be described for the free energy competition between bcc spheres, hexagonal-packed cylinders, lamellae, and ordered-bicontinuous double-diamond, as a function of composition, arm number and molecular weight; the model used for the double-diamond morphology is one of the constant-mean-curvature-interface structures of the 'D' family discovered in the applicant's thesis. The general approach was introduced by Leibler [1980], and his predictions of phase behavior and scattering curves in the weak-segregation limit have been shown to agree well with experiments [Mori et al. 1985].

Beginning with equation 3.14 in Ohta and Kawasaki, the bilinear term in the free energy was evaluated using Fourier transforms, where the integration becomes a summation because the Fourier transform of a periodic function consists of delta-functions at reciprocal lattice vectors. The static structure factor that is equation (28) in de la Cruz and Sanchez (which reduces to equation 3.15 of Ohta and Kawasaki when n=1) was used in its exact form; the $q^2$ term remains the same as that in 3.19 of Ohta and Kawasaki for any arm number n, while the function s(f) of 3.19, which gives the constant in the asymptotic behavior for large q, can be calculated to be:

$$s(f) = 1 - (n-1)(1-f)/2 + f(1-f)(n-3)/2.$$

These two terms were subtracted off from the expression (28) since they are included in the short-range free energy contribution in the analysis of Ohta and Kawasaki. The long-range contribution is then evaluated by summing, over all reciprocal lattice vectors, the product of the resulting expression with the square of the form factor; (see Equation 1, FIG. 7) the corresponding term in Ohta and Kawasaki's formulation is the A(f) term in equation 3.20 that is multiplied by the square of the form factor. Clearly it is a considerable improvement to use the exact expression (3.15 for linear diblocks, and (28) in de la Cruz and Sanchez for stars), rather than the approximation 3.19 which matches the exact expression only to an accuracy of 4% and has the wrong asymtotic behavior for large q; this can easily be accomplished since the integral becomes a summation in reciprocal space and the series converges rapidly. Note that this approach is equivalent to Ewald's method in the limit of large G. After the summation to yield the long-range free energy contribution, the surface area per unit volume yields the short-ranged contribution just as in Ohta and Kawasaki (using their approximation that the interfacial tension is the same for all morphologies), and the total energy is minimized over the lattice parameter.

It remains to describe the calculation of the form factor for the double-diamond structure; the form factors of spheres, cylinders, and lamellae are all well-known. By using the divergence theorem, the volume integration can be reduced to an integration over the surface [Hosemann and Bagchi 1962], as shown by equation 2 in FIG. 7.

The surface in the finite element solution is represented by triangular patches (much as in a geodesic dome), and because the normal direction is fixed over a given triangle in space, this integral can be done analytically over every patch. The surface integral in equation (2), evaluated over a triangle in which the x-y-z coordinates of the three vertices are given by (x1, y1, z1), (x2, y2, z2), and (x3, y3, z3) is shown by equation 3 in FIG. 7.

A fundamental patch of the surface was represented by 800 such triangular patches; a unit cell of surfaces can be broken down into 24 identical fundamental patches. The from factor calculated in this way is mathematically exact for the structure so represented. The applicant's thesis contains demonstrations of the accuracy of the finite element representation of these constant-mean-curvature surfaces.

In the Appendices are reproduced the computer codes used for 1) the computation of the form factor from the surface (Appendix A); and 2) the summation in reciprocal space and final computation of the total free energy for the candidate structures (Appendix B). The bcc spheres were omitted because they are favored only for small values of the volume fraction f (<0.22), and the double-diamond occurs at values of f (or of 1−f) near f=0.3.

The results of the theory are now given for a volume fraction of f=0.644 (the volume fraction for the surface with mean curvature equal to 1.6), as a function of arm number; this is the volume fraction of the inner or core blocks of the star. There is also a dependence on molecular weight (which is not predicted by Ohta and Kawasaki because of their use of the approximated structure factor), and this is described by the parameter N which is the product of the square of the Kuhn step length with the number of Kuhn steps in a single arm, divided by 6. In the experiments of Thomas et al. [1986], the unit cell was on the order of 30 nm, and the statistical Kuhn length on the order of 1 nm, so that in dimensionless units this length is 0.033, and since the polymer index was about 160, a good value for this parameter is 0.03. The free energies of the candidate morphologies, as a function of arm number, are as follows:

| arm number | D-Diamond | Lamellar | Cylindrical |
|---|---|---|---|
| 1 | 1.107211 | 1.076124 | 1.074017 |
| 2 | 1.060160 | 1.049548 | 1.048806 |
| 3 | 1.042949 | 1.041448 | 1.041374 |
| 4 | 1.037309 | 1.039309 | 1.039511 |
| 5 | 1.037388 | 1.039869 | 1.040130 |
| 6 | 1.040689 | 1.041883 | 1.042074 |

These energies are in the same units as those in Ohta and Kawasaki. Thus it is seen that double-diamond is calculated to occur at higher arm numbers, as was observed in the experiments of Thomas et al.

The key to these results is that no assumptions were made about the specific chemistry of the copolymer, such as the interaction parameter, as long as this interaction parameter is large enough for the strong-segregation assumption to be valid. Thus the ordered bicontinuous double-diamond morphology is predicted to occur in a wide variety of block copolymer systems. It should be emphasized again that the statistical mechanical treatment underlying this theory has been shown to agree well with experiments.

Conversion of neutral polymers to ionomers.

The commercial importance of ionomeric polymer membranes has stimulated research on methods of converting neutral polymers to ionomers, both before the formation of a membrane and as a post membrane-formation step. Methods of incorporating ionomers into membranes with triply-periodic submicron porespaces have been described in this section and include:

a) conversion of a neutral polymer membrane produced by polymerization of a component of a small-molecule triply-periodic phase via a process of type 1);

b) formation of a triply-periodic phase incorporating an ionogenic polymer above its melting point, followed by subsequent solidification of the polymer;

c) infiltration of a (low porosity) triply-periodic membrane with either an ionomer (above its melt temperature), or a monomer that can be polymerized, and modified if necessary, to form an ionogenic polymer; and d) formation of a triply- periodic morphology with a block or graft copolymer one component of which is ionomeric.

The two most important classes of ionomeric polymers in membranology are the styrene-type and perfluorinated ionomers, and the primary focus of this part will be on these, although other classes of ionomers may be found to be compatible with the types of processes described herein. Reactions for grafting ionogenic polymers or oligomers to neutral polymers will be briefly discussed; such reactions are the subjects of investigations in present-day polymer research and promise to open up new possibilities for the grafting of ionogenic polymers in a post membrane formation process. In addition, such graft copolymers might be used as the basis for type 2) processes, for recent evidence [Hasegawa 1986] indicates that graft copolymers can form bicontinuous cubic phases.

Styrene polymers, and copolymers with, for example divinyl benzene and/or ethyl vinyl benzene, are excellent starting materials for the formation of ionomers, because of the reactivity of the aromatic rings for chloromethylation, nitration, and particularly sulfonation. Such polymers can be converted to strong acids by sulfonation with sulfuric or chlorosulfonic acid, and this can be followed by conversion to the sodium form by addition of a slight excess of alkali. Weak-acid cation exchange polymers can be made by with acrylic or methacrylic acids, as mentioned above. These reactions can be performed after the formation of the membrane with the neutral polymer.

Strong-base anionic-exchange polymers can also be produced from styrene-based polymers or copolymers in a post membrane-formation step. Chloromethylation by methyl chloromethyl ether, followed by amination with a tertiary amine, yields strong-base polymers even in pure polystyrene. Amination of the same chloromethylation product with primary or secondary amines yields weak-base anion-exchange polymers. Redox membranes, which are oxidation and reduction agents lacking actual charged groups, can be produced by addition polymerization of styrene, divinyl benzene, and esterified hydroquinone.

Perfluorinated ionomers are presently the most important cation-exchange membrane polymers, primarily because of their strength and chemical stablility. As an example of the possibilities of production of these types of ionomers, consider starting with a copolymer of tetrafluoroethylene and perfluoro-3,6-dioxa-4-methyl-7-octene-sulfonyl fluoride. The sulfonate groups can be converted to the sulfonic acid form by nitric acid, after which oxidation in n-butyl alcohol followed by hydrolysis with sodium hydroxide yields a polymer suitable for use as an electrolysis membrane. Reaction with vaporous phosphorous pentachloride followed by treatment with triethylamine and immersion in a solution of water, dimethyl sulfoxide and potassium hydroxide, or by treatment with aqueous ammonia, also yield ionomeric polymers suitable for electrolysis. Polyol surfactants can be subjected to reactions that induce an ionic character. The terminal hydroxyl groups can be converted to various functional groups [Lundsted and Schmolka 1981], such as to a halide and subsequently to a tertiary amine by reaction with a substituted amine. This in turn can be converted to an amine oxide, by reaction with hydrogen peroxide, or to a cationic quaternary surfactant by reaction with an alkylating agent. Polyurethane can be obtained by reacting with diisocyanate. Anionic surfactants can be produced by addition of epichlorohydrin and sodium sulfite, or by reaction with an oxygen-containing acid or acid anhydride. And cationic surfactants can also be produced from block copolymeric surfactants by reaction with ethylene or propylenimine, or by methylation.

A great deal of recent research has focused on conducting polymeric membranes. Electroactive polymer films have been produced by electropolymerization of aromatic heterocyclic compounds [Diaz et al. 1983]. Highly conducting membrane polymers have been produced by iodine-doping [Schechtman and Kenney 1983], and by electrochemical reactions [Huq et al. 1983]; in fact, polyacetylene can be reduced or oxidized to compositions that have the electronic properties of metals.

Grafting of neutral but potentially ionomeric materials onto neutral membrane polymers, particularly as a post membrane-formation step, is another proven source of ionomeric membranes. Polyacrylate ester can be grafted onto cellophane, and subsequently hydrolyzed to produce a weak-acid cationic-exchange membrane. Similarly polystyrene has been grafted onto polyethlyene and sulfonated, to form a strong-acid cationic-exchange membrane. For post membrane formation grafting reactions, the creation of free radicals on the pore surfaces to act as initiation sites for polymerization of added monomers is attractive, in that monomers could diffuse easily to these sites. Free radicals can be produced for grafting sites by peroxides or redox catalysts, or by exposure to electrons, gamma rays or UV radiation.

Industrial Applicability

As previously mentioned, the past 20 years has seen tremendous growth in the applications of polymeric membranes, not only in filtration—microfiltration (MF), ultrafiltration (UF), and hyperfiltration or reverse osmosis (RO)—but also in a variety of other areas such as fuel cells and batteries, controlled-release devices as for drug or herbicide metering, dialysis and electrodialysis, pervaporation, electrophoresis, membrane reactors, ion-selective electrodes, and as supports for liquid membranes, to name some important areas. Furthermore, modification of neutral polymer membranes can yield ionomeric or 'ion-exchange' membranes which are finding increasing application in many chemical, electrochemical, filtration and even biochemical processes. In many applications the availability of a membrane of the type described herein with precisely-controlled porespace and high porosity represents a significant technological advance.

Traditionally membranes have been associated with filtration processes for purification or concentration of fluids, or recovery of particles as in the recovery of colloidal paint particles from spent electrolytic paint particle suspensions, and the very important application of recovering of lactose-free protein from whey. The use of reverse osmosis and electrodialysis in removing trace pollutants from industrial waste streams is increasing each year, as the cost of these processes is often less than other alternatives [Spatz 1981]; because these processes are being applied for waste treatment in agricultural, chemical, biochemical, eletrochemical, food, pharmaceutical, petrochemical, and pulp and paper industries, the development of this technology will have a significant impact on the environment.

The earliest, and still the most frequently mentioned, use of RO (also known as hyperfiltration) is in the desalination of salt water and brackish. Desalinated water obtained from RO of seawater could be an important solution to the fresh water shortages that are projected over the next few decades. The literature on desalination by RO is extensive. From the point of view of the present invention, the two characteristics that distinguish the RO membrane from UF and MF membranes—namely smaller pore size (less than 10 Angstrom) and lower porosity—would result from the polymerization of the surfactant of a binary surfactant/water bicontinuous cubic phase. As discussed earlier, the very concept of bicontinuity first arose in experiments on binary surfactant/water cubic phases, and there are now many such binary cubic phases believed to be bicontinuous, most of which occur near 50% volume fraction water and with channel diameter less than 4 nm. Alternatively, RO membranes of intermediate porosity, roughly 70%, would result from chemical erosion of one component of a block copolymer cubic phase of low molecular weight. In his discussion of RO membranes, Kesting [1985] lists narrow pore size distributions as the first criteria for an effective membrane.

Reverse osmosis is finding new applications every year. RO and UF are being investigated [Drioli et al. 1981] for the treatment of must and wines without the addition of sulfur dioxide, which is routinely added to remove certain enzymes that would otherwise cause an oxidized taste. The concentration of tomato juice by RO has been applied on a semicommercial scale, and results in enhanced taste and color over conventional processes [Ishii et al. 1981]. A recent study [Farnand et al. 1981] has shown that RO can also be used to separate inorganic salts from nonaqueous solvents such as methanol; the latter solvent is of particular importance in that methanol is being investigated as an alternative fuel.

As pointed out by Spatz [1981], there is in reality no fine line between RO membranes and UF membranes, but rather the pore size in the UF membrane is generally larger, so that the UF membrane does not reject small molecule salts as does the RO membrane. A typical UF membrane will reject over 99% of the organics over 200 molecular weight and over 98% of monosaccharides such as dextrose and glucose. Size fractionation is the basis of many UF processes, and narrow pore size distributions are often critical, as in hemofiltration for the treatment of renal failure [Kai et al. 1981]; the increased discrimination of hemofiltration with UF membranes over that of hemodialysis with respect to the rejection of solutes larger than uric acid has been proposed as the reason for the success of hemofiltration for hemodialysis-difficulties patients.

Ultrafiltration is of importance in the separation of viruses, which by virtue of the fact that they are much smaller than bacteria generally pass through microfiltration membranes, unless the latter are treated so as to be positively charged [Brock 1983]. This leads to failure when contaminants neutralize the charge, after which the retention or passage will depend only on the pore size [Raistrick 1982]. The virus known as human T-lymphotropic virus III (HTLV-III; also called human immunodeficiency virus or HIV) is a sphere of diameter roughly 1,000 Angstroms, now believed to be responsible for the disease AIDS as well as other neurological disorders and perhaps even the cancers. The potential importance of a membrane of the type disclosed herein is demonstrated by the fact that some hemophiliacs developed AIDS after receiving infusions of a plasma preparation called Factor VIII, which had been passed through a filter that was fine enough to remove bacteria but not virus particles [Gallo 1987].

In dialysis, solute permeates through a membrane from a more concentrated to a less concentrated solution; thus it differs from UF in that in the latter the solute flux is coupled to the solvent flux. The dialysis of blood to remove urea and creatinine from uremia patients, known as hemodialysis, is believed to be presently the largest single application of membranes to separations. Dialysis is also used in the pharmaceutical industry to remove salts, in the rayon industry, and in the metallurgical industry to remove spent acids. Since dialysis membranes are generally very finely porous—with molecular weight cutoffs of around 1,000—the present invention could be applied in these areas; in the case of hemodialysis, where human suffering is involved, advantages offered by a more precisely controlled membrane could well justify a higher cost, if the present invention were more expensive than the extruded cellulose hydrogels that are presently used.

Another medical application for membranes is in controlled drug-delivery systems. The simplest description of these is that a drug is imbibed into the pores of a membrane, and released slowly so as to approximate a constant concentration over time in the body (zero-order release), or a concentration that fluctuates in response to physiological conditions (first-order release). In some cases biodegradable polymers are used, such as lactic acid and glycolic acid homopolymers and copolymers. In the case of first-order systems for the release of insulin in the treatment of diabetes, a glucose-sensitive membrane is being investigated [Kost 1987] in which the enzyme glucose oxidase is immobilized in a poly-N,N dimethylamino-methyl methacrylate/poly-HEMA copolymer. So far the membrane has shown the ability to release ethylene glycol in response to glucose concentration, but porosity of greater than 50% is required to release insulin. Some other drugs which are being investigated for membrane release are nitroglycerine, progesterone, and epinephrine, to name only a few examples. The importance of high porosity and therefore high concentration in the membrane, and of well-defined pores has lead to the use of phase-inversion membranes prepared by the so-called thermal process; the diameters of the cells in these membranes are between 1 and 10 microns, with porosities of roughly 75%. Membrane metering devices are potentially of great utility in the release of other effectors such as fragrances, insecticides, and herbicides.

Polymer UF membranes provide supports for liquid membranes, in which the liquid is immobilized in the porespace of the solid microporous membrane by capillarity. The immobilized liquid membrane offers the advantages over solid membranes of higher diffusivities, higher solubilities, and in many cases very high selectivity. Concentrated $CsHCO_3$ aqueous solutions can be use to recover carbon dioxide from gaseous mixtures [Ward 1972]. Liquid membranes are also used to recover carbon dioxide from the products of carbon dioxide-based tertiary oil recovery methods, and to remove ammonia from wastewater. Immobilized liquid membranes have been proposed for the removal of toxic materials such as dichromate ions from electroplating rinsewaters [Smith et al. 1981]. UF membranes also provide possible supports for so-called dynamically-formed membranes. The homogeneity of such a membrane is highly dependent on the degree of order in the porespace of the support; carbon black has been used but due to the presence of large pores, the homogeneity and permselectivity have not been good. The two most important physical characteristics of the most desirable support would be a high degree of order and a pore size less than 1 micron, both of which are satisfied by the present invention. Dynamically-formed membranes can be used to separate small molecules and ions, and have been shown to be effective in the desalination of water [Kraus et al. 1967].

Chromatography is a separations process that is of great importance in analytical chemistry. In gel-permeation chromatography (GPC), separation of chemical mixtures is based on differences in passage times through a mobile liquid phase filled with porous polymeric particles. Separations on the basis of molecular weight could be enhanced by a polymer with monodisperse pores.

Pervaporation is a membrane-based separations process capable of separating complex azeotropic mixtures. It also circumvents the problem in RO of high osmotic pressures that oppose flux in attempts to concentrate a solute to high purity. Pervaporation has been shown to be capable of separating linear hydrocarbons from olefins, and from branched hydrocarbons [Binning et al. 1961]. Thus interest in membranes with precisely controlled porespaces has arisen in the petroleum industry. Diffusion of the components through the membrane is the rate-limiting step, and thus high porosity and uniform pores are important in pervaporation as well as in the recent modification of the process known as membrane-aided distillation.

Electrophoresis is a separations process for macromolecules such as proteins which is based on an imposed electric field, where a porous membrane must be used to frustrate remixing via thermal convection. Finely porous membranes such as agarose or polyacrylamide gels with pore sizes on the order of 1,000 Angstroms result in enhanced separation over that of cellulose acetate membranes with pores on the order of 1 micron, due to a combination of both the electrophoretic effect and sieving. Electrophoresis is an important tool today in biological and bioengineering research, and it is anticipated that it will be realized in large scale separations processes, and in three dimensions, in the near future. Certainly in cases where sieving is a significant contribution to the separation, a membrane with triply-periodic submicron pores may be of importance.

The applicant has demonstrated [Anderson 1986] that the progressions of structures that occur in phases of cubic symmetry should also include structures that consist of interconnected sphere-like domains, which would be the perfect geometry for an electrophoresis membrane. The electron micrograph of FIG. 2, and the model structures in FIG. 4 indeed indicate an interconnected-sphere structure. Also, the model that is to date the best model for the cubic phase occuring in the star-block copolymers of Thomas et al. 1986] is based on a surface of constant mean curvature from the author's thesis which is shown in the thesis to be very accurately described by interconnected, nearly-spherical domains. At present, studies are underway to determine more precisely the exact shape of the domains. FIG. 5 shows the comparison between a (digitized) electron micrograph of a star-block copolymer cubic phase and the theoretical prediction from the constant-mean-curvature-interface model.

Selective membrane electrodes are chemically-specific probes in which a reference electrode is separated from the test solution by a selective membrane; the species to be detected diffuses through the membrane and reacts so as to produce an ion that is measured by an ion-selective electrode. A wide variety of membranes is used, including both neutral and ionomeric membranes, and enzymes immobilized in microporous membranes. Selective membrane electrodes are used to detect carbon dioxide in blood and fermentation vats, ammonia in soil and water, sulfur dioxide in stack gases, foods, and wines, sulfur in fuels, nitrite in foods, and hydrogen cyanide in plating baths and waste streams, for some examples.

Ionomeric Membranes

Methods have been described herein for fabricating ionomeric, or 'ion-exchange' membranes with the triply-periodic porespaces that distinguish this invention. In view of the fact that the surface area of the membrane analyzed earlier is 3500 sq. meters/gram, such a membrane would be of potential impact in the general field of ion-exchange membranes and resins—in particular in applications where precise porespace characteristics are required, such as when ion-exchange or electromembrane processes are enhanced by or combined with sieving. As in the case of neutral membranes, the field of ion-exchange membranes and resins is large and ever-expanding, so that only a brief overview of the applications with respect to the present invention can be given here.

Electrodialysis is the most important electromembrane process, used in the concentration or removal of electrolytes, metathesis reactions, and the separation of electrolysis products. Ion replacement is also important in, for example, citrus juice sweetening where citrate ions are replaced by hydroxyl ions. Electrodialysis for ion-exchange of $Na+$ to $Ca+$, $K+$, or $Mg+$ is being investigated as a source of low-sodium milk. Because the resistance to solvent flow is important in problems of anomalous osmosis and incongruent salt flux, a membrane with uniform pores would enhance the predictibility of the process. Although there is debate about the exact origin of anomalous osmosis [Schlogl 1955], there is some evidence that it is due at least in part to inhomogeneities in the porespace [Sollner 1932]. Also, electrical conductance is lower in heterogeneous membranes than in homogeneous polystyrene-based membranes, for example [Kedem and Bar-On 1986].

Ion-exchange membranes are used in batteries in part because their electrical conductances are higher than in the silver halides of conventional solid-electrolyte cells. They are also used in fuel cells such as the Bacon cell, in which hydrogen and oxygen are combined to form water with the release of heat and electricity. Efficiencies of these chemical reactions can approach 100%. Because of the high reactivity of hydrogen, the Bacon cell can be operated at relatively low temperatures, opening up the possibiliity of using an ion-exchange membrane as as solid-state electrolyte. The ideal electrolyte would be permeable to only one ionic species, and if this were to be accomplished or aided by membrane sieving, very uniform pores would be required. In view of this, and of the other advantages offered by membrane electrolytes over metal electrolytes such as small unit thickness, immunity to carbon dioxide impurities in the hydrogen feed, and the ability of the membrane to also serve as the gas separator, the present invention could prove to be the best possible electrolyte in such a cell.

Both neutral and ionomeric membranes of the type described herein could be used in a variety of other reactions, for example by doping the membrane with a catalyst or by controlling the reaction rate precisely by diffusion limitation. The large specific surface, 3500 sq. m./gm, and highly-controlled diffusion paths and reaction sites could allow for a greater degree of control than has been possible with prior art membranes.

Appendix A - (Form Factor Program - FORTRAN Code)

```
c     Uses Hosemann surface-integral method!
c     This is for 21x21 meshes!!
c     calculates form factor of a LFR of double diamond at
c     reciprocal space lattice vectors. Face centered
c     real space lattice used. Note that densities are
c       1-phi(in channels), -phi(in matrix), (and 0 outside LFR).
      parameter(nn=2)
      parameter(nnp=3)
      implicit double precision(a-h,p-z)
      dimension q(441),for(nn,nnp,nnp)
     2,j(3),amp(nn,nnp,nnp),h1(24,nn,nnp,nnp)
     3,h2(24,nn,nnp,nnp),h3(24,nn,nnp,nnp)
      dimension fv(3),x(441),y(441),z(441)
      pi=4.*atan(1.0)
      dd=.05 open(unit=4,file='d3p8f')
      open(unit=9,file='fo3p8a')
      fv(1)=1.0
      fv(2)=.33698
      fv(3)=.3560112
      nbum=0
      do 999 nd=1,1
      vf=fv(nd)
c     vf=1.0
      vfm=1.0-vf
      read(4,4)(q(nm),nm=1,441)
  4   format(3e26.14)
      do 5 jj=1,nn
      do 3 kk=0,nn
      do 1 ll=0,nn
      amp(jj,kk+1,ll+1)=0.0
c     Note that actual Miller indices of for(jj,kk+1,ll+1)
c       are 2*jj,2*kk,2*ll, with fcc unit cell.
  1   continue
  3   continue
  5   continue
      do 20 n=1,21
      do 10 m=1,21
      nns=21*(n-1)+m
```

```
      ww=q(nns)
      uu=(m-1)*dd
      vv=(n-1)*dd
      x(nns)=.25*(uu-(uu+vv)*ww)+.25
      y(nns)=.25*(-uu+(uu-vv)*ww)+.25
      z(nns)=.25*(uu+(2.-uu-vv)*ww)-.25
c     Probly need to change .5 to .25 here.
c     x(nns)=0.5*(uu+ww*(1.+vv-uu))-0.25
c     y(nns)=0.5*(uu+ww*(1.-uu-vv))-0.25
c     z(nns)=0.5*(-uu+ww*(1.-vv+uu))-0.25
   10 continue
   20 continue
      do 51 jk1=1,nn
      do 40 jk2=0,jk1
      do 30 jk3=0,jk2
      j(1)=jk1
      j(2)=jk2
      j(3)=jk3
      do 31 n3=1,3
      do 29 n2=1,2
      mm1=2*n2-3+4*(2-n2)+n3
      m1=mm1-3*((mm1-1)/3)
      mm2=4*n2-6+4*(2-n2)+n3
      m2=mm2-3*((mm2-1)/3)
      mm3=6*n2-9+4*(2-n2)+n3
      m3=mm3-3*((mm3-1)/3)
c              Loop over 4 inversions.
      do 19 jb=1,4
      if(jb.eq.4)go to 43
      if(jb.eq.3)go to 33
      if(jb.eq.2)go to 23
      xm=1.0
      ym=1.0
      zm=1.0
      go to 93
   23 xm=-1.0
      ym=-1.0
      zm=1.0
      go to 93
   33 xm=-1.0
      ym=1.0
      zm=-1.0
      go to 93
   43 xm=1.0
      ym=-1.0
      zm=-1.0
c     Note that wave vector is 2*pi*(2m1,2m2,2m3)
   93 numh=6*(jb-1)+3*(n2-1)+n3
      h1(numh,j(1),j(2)+1,j(3)+1)=4.*pi*j(m1)*xm
      h2(numh,j(1),j(2)+1,j(3)+1)=4.*pi*j(m2)*ym
      h3(numh,j(1),j(2)+1,j(3)+1)=4.*pi*j(m3)*zm
   19 continue
   29 continue
   31 continue
   30 continue
   40 continue
```

```
   51 continue
      do 200 nv=1,20
      do 100 nu=1,20
      iflag=1
      nl=21*(nv-1)+nu
      n1=nl
      n2=nl+1
      n3=nl+22
   50 x1=x(n1)
      x2=x(n2)
      x3=x(n3)
      y1=y(n1)
      y2=y(n2)
      y3=y(n3)
      z1=z(n1)
      z2=z(n2)
      z3=z(n3)
      a1=x3-x2
      a2=y3-y2
      a3=z3-z2
      b1=x1-x2
      b2=y1-y2
      b3=z1-z2
      r1=a2*b3-a3*b2
      r2=a3*b1-a1*b3
      r3=a1*b2-a2*b1
      em=dsqrt(r1*r1+r2*r2+r3*r3)
      en1=r1/em
      en2=r2/em
      en3=r3/em
      do 73 k1=1,nn
      do 72 k2=0,k1
      do 71 k3=0,k2
      ksum=k1+k2+k3
      neven=ksum-2*(ksum/2)
      do 70 nf=1,24
      hh1=h1(nf,k1,k2+1,k3+1)
      hh2=h2(nf,k1,k2+1,k3+1)
      hh3=h3(nf,k1,k2+1,k3+1)
      a=x2*hh1+y2*hh2+z2*hh3
      b=a1*hh1+a2*hh2+a3*hh3
      c=b1*hh1+b2*hh2+b3*hh3
      eps=en1*hh1+en2*hh2+en3*hh3 if(abs(b).lt.0.0000001)go to 105
      if(abs(b-c).lt.0.0000001)go to 109
      if(abs(c).lt.0.0000001)go to 101
      if(neven.eq.0)go to 81
   80 amp(k1,k2+1,k3+1)=amp(k1,k2+1,k3+1)+em*eps
     2*((cos(a+b)-cos(a+c))/(b*(c-b))
     3-(cos(a)-cos(a+c))/(b*c))
      go to 70
   81 amp(k1,k2+1,k3+1)=amp(k1,k2+1,k3+1)+em*eps
     2*((sin(a+b)-sin(a+c))/(b*(c-b))
     3-(sin(a)-sin(a+c))/(b*c))
      go to 70
```

```
101 if(neven.eq.0)go to 102
   amp(k1,k2+1,k3+1)=amp(k1,k2+1,k3+1)+
   2em*eps*((cos(a)-cos(a+b))/b**2-sin(a)/b)
   go to 70
102 amp(k1,k2+1,k3+1)=amp(k1,k2+1,k3+1)+
   2em*eps*((sin(a)-sin(a+b))/b**2+cos(a)/b)
   go to 70
105 if(abs(c).lt.0.0000001)go to 111
   if(neven.eq.0)go to 106
   amp(k1,k2+1,k3+1)=amp(k1,k2+1,k3+1)+
   2em*eps*((cos(a)-cos(a+c))/c**2-sin(a)/c)
   go to 70
106 amp(k1,k2+1,k3+1)=amp(k1,k2+1,k3+1)+
   2em*eps*((sin(a)-sin(a+c))/c**2+cos(a)/c)
   go to 70
109 if(abs(c).lt.0.0000001)go to 111
   if(neven.eq.0)go to 110
   amp(k1,k2+1,k3+1)=amp(k1,k2+1,k3+1)+
   2em*eps*(sin(a+b)/b+(cos(a+b)-cos(a))/b**2)
   go to 70
110 amp(k1,k2+1,k3+1)=amp(k1,k2+1,k3+1)+
   2em*eps*(-cos(a+b)/b+(sin(a+b)-sin(a))/b**2)
   go to 70
111 if(neven.eq.0)go to 113
   amp(k1,k2+1,k3+1)=amp(k1,k2+1,k3+1)-
   2em*eps*sin(a)
   go to 70
113 amp(k1,k2+1,k3+1)=amp(k1,k2+1,k3+1)+
   2em*eps*cos(a)
 70 continue
 71 continue
 72 continue
 73 continue
   if(iflag.gt.1)go to 100
   iflag=2
   n1=nl+22
   n2=nl+21
   n3=nl
   go to 50
100 continue
200 continue
c  print *, nbum
   do 994 jj1=1,nn
   do 993 jj2=0,jj1
   do 992 jj3=0,jj2
   hsq=4.*pi*pi*float(jj1*jj1+jj2*jj2+jj3*jj3)
   am=.5*amp(jj1,jj2+1,jj3+1)/hsq
   write(9,9)jj1,jj2,jj3,am
 9 format(3i5,2e20.8)
992 continue
993 continue
994 continue
999 continue
   write(9,176)nbum
176 format(i12)
   end
```

```
1  0  0   -0.54926312E-20
1  1  0    0.25172142E-01
1  1  1    0.15840510E-01
2  0  0   -0.22002978E-02
2  1  0   -0.21970525E-20
2  1  1   -0.23877252E-02
2  2  0    0.98843060E-03
2  2  1    0.32189144E-02
2  2  2   -0.73791965E-02
      0
```

Appendix B - (Total Free Energy Program - FORTRAN Code)

```
c This program computes, from the form factor
c of a Double-diamond surface, the total free
c energy for the double-diamond, lamellar,
c and cylindrical morphologies.
c
      implicit double precision(a-h,o-z)
      double precision MMBSJ1
      dimension al(2),ef(2),d(2)
      external MMBSJ1
      open(unit=4,file='forless')
      pi=4.*atan(1.0)
      th=1./3.
      con=12.**th
      print *, 'enter (real) N0, and arm#'
      read *, en0,arm
      do 100 mp=1,4
      nmax=1769
      print *, 'enter f and area'
      read *, f,area
      en=en0
      ff=f*(1.-f)
      al(1)=f
      al(2)=1.-f
      sf=1.-.5*(arm-1.)*al(2)+.5*ff*(arm-3.)
      sum=0.0
      do 90 nd=1,nmax
      read(4,4)j,k,l,for
 4    format(3i5,e20.8)
      np=2
      nq=2
      nr=6
      if(k.eq.0)np=1
      if(l.eq.0)nq=1
      if(j.eq.k)nr=3
      if(k.eq.l)nr=3
      if(j.eq.l)nr=1
      mult=2*np*nq*nr
      qs=4.*pi*pi*float(j*j+k*k+l*l)
      x0=en0*qs/2.
      do 5 mm=1,2
      u=al(mm)*x0
      d(mm)=al(mm)*al(mm)*(2./u**2)*
 2    (u+exp(-u)-1.)
      ef(mm)=(1.-exp(-u))*al(mm)/u
```

```
      5 continue
        ep=exp(-al(1)*x0)
        gq=(d(1)+d(2)+(arm-1.)*(ef(1)*ef(1)+
       2ef(2)*ef(2)*ep*ep)+2.*ef(1)*ef(2)*(1.+
       3(arm-1.)*ep))/
       4(en0*en0*(d(1)*d(2)+(arm-1.)*(d(2)*ef(1)
       5*ef(1)+d(1)*ef(2)*ef(2)*ep*ep)-(ef(1)*ef(2))
       6**2*(1.+2.*(arm-1.)*ep)))
        fac=gq*en*en*en*ff*ff/3.-en*en*qs*ff/12.
       2-en*sf/6.
        sum=sum+mult*for*for*fac
     90 continue
        encub=(16.*sum)**th*con*area**(2.*th)/f
        print *, 'Energy for double-diamond = Q* :'
        print *, encub
c
c Now do lamellar phase
c
        mmax=1769
        sum=0.0
        do 95 nd=1,mmax
c Enter form factor here***.
        for=sin(pi*nd*f)/(pi*nd)
c Note that wave vector is 2*pi/D *(nd,0,0)
        qs=4.*pi*pi*float(nd*nd)
        x0=en0*qs/2.
        do 6 mm=1,2
        u=al(mm)*x0
        d(mm)=al(mm)*al(mm)*(2./u**2)*
       2(u+exp(-u)-1.)
        ef(mm)=(1.-exp(-u))*al(mm)/u
      6 continue
        ep=exp(-al(1)*x0)
        gq=(d(1)+d(2)+(arm-1.)*(ef(1)*ef(1)+
       2ef(2)*ef(2)*ep*ep)+2.*ef(1)*ef(2)*(1.+
       3(arm-1.)*ep))/
       4(en0*en0*(d(1)*d(2)+(arm-1.)*(d(2)*ef(1)
       5*ef(1)+d(1)*ef(2)*ef(2)*ep*ep)-(ef(1)*ef(2))
       6**2*(1.+2.*(arm-1.)*ep)))
        fac=gq*en*en*en*ff*ff/3.-en*en*qs*ff/12.
       2-en*sf/6.
        sum=sum+for*for*fac
     95 continue
        sum=sum*24.
        enlam=sum**th/f
        print *, '*'
        print *, 'Lamellar energy = Q* :'
        print *, enlam
c Now compute total energy
c for cylindrical phase
        sr3=sqrt(3.)
        rad=sqrt(2.*f/(pi*sr3))
        nmax=64
        sum=0.0
        do 89 ne=1,nmax
        do 80 nd=0,ne
```

```
      ns=2
      nb=2
      if(ne.eq.ns)nb=1
      if(nd.eq.0)ns=1
      amult=float(2*ns*nb)
c Enter form factor here***.
      argg=rad*2.*pi*sqrt(float(nd*nd+nd*ne+ne*ne))
      bes=MMBSJ1(argg,ier)
      for=f*bes/argg
c Note that wave vector is 2*pi*(nd,ne,0)
c
      qs=argg*argg/rad**2
      x0=en0*qs/2.
      do 15 mm=1,2
      u=al(mm)*x0
      d(mm)=al(mm)*al(mm)*(2./u**2)*
     2(u+exp(-u)-1.)
      ef(mm)=(1.-exp(-u))*al(mm)/u
   15 continue
      ep=exp(-al(1)*x0)
      gq=(d(1)+d(2)+(arm-1.)*(ef(1)*ef(1)+
     2ef(2)*ef(2)*ep*ep)+2.*ef(1)*ef(2)*(1.+
     3(arm-1.)*ep))/
     4(en0*en0*(d(1)*d(2)+(arm-1.)*(d(2)*ef(1)
     5*ef(1)+d(1)*ef(2)*ef(2)*ep*ep)-(ef(1)*ef(2))
     6**2*(1.+2.*(arm-1.)*ep)))
      fac=gq*en*en*en*ff*ff/3.-en*en*qs*ff/12.
     2-en*sf/6.
      sum=sum+for*for*fac*amult
   80 continue
   89 continue
      sum=sum*24.
      encyl=(3.*sum/(f*rad*rad))**th
      print *, '*'
      print *, 'Cylindrical energy = Q* :'
      print *, encyl
      print *, '*'
  100 continue
      end
```

APPENDIX C

References

Alward, D. B., D. J. Kinning, E. L. Thomas and L. J. Fetters 1986 Macromolecules 19, 215.

Anderson, D. M. 1986 Ph. D. thesis, Univ. of Minnesota.

Anderson, D. M., S. M. Gruner and S. Leibler (work in progress).

Balmbra, R. R., J. S. Clunie and J. F. Goodman 1969 Nature 222, 1159.

Barrer, R. M. 1978 Zeolites and clay minerals as sorbents and molecular sieves, Academic Press, London.

Balmbra, R. R., J. S. Clunie and J. F. Goodman 1969 Nature 222, 1159.

Baughman, R. H., H. Eckhardt, R. E. Elsenbaumer, R. R. Chance, J. E. Frommer, D. M. Ivory, G. G. Miller and L. W. Shacklette 1983 in Proceedings of the symposium on membranes and ionic and electronic conducting polymers, May 17–19, 1982 Case Western Reserve University, The Electrochemical Society, N.J.

Binning, R., R. Lee, J. Jennings and E. Martin 1961 Ind. Eng. Chem. 53, 45.

Blum, F. D., S. Pickup, B. Ninham and D. F. Evans 1985 J. Phys. Chem. 89, 711.

Brock, T. D. 1983 Membrane filtration: a user's guide and reference manual, Science Tech, Inc. Madison, Wis. Data on page 57 courtesy of Oxoid Ltd., Basingstoke, England.

Bull, T. and B. Lindman 1974 Mol. Cryst. Liq. Cryst. 28, 155.

Charvolin, J. 1985 J. de Physique 46, C3-173.

Chen, S. J., D. F. Evans, B. W. Ninham, D. J. Mitchell, F. D. Blum and S. Pickup 1986 J. Phys. Chem. 90, 842.

Danielsson, I. and B. Lindman 1981 Colloids and Surfaces 3, 391.

de la Cruz, M. O and I. C. Sanchez 1986 Macromolecules 19, 2501.

Diaz, A. F., J. Bargon and R. Waltman 1983 in Proceedings of the symposium on membranes and ionic and electronic conducting polymers, May 17–19, 1982 Case Western Reserve University, The Electrochemical Society, N.J.

Drioli, E, G. Orlando, S. D'Ambra and A. Amati 1981 in Synthetic membranes, vol. II, A. F. Turbak, ed. ACS Symposium Series, Wash. D.C.

Farnand, B. A., F. D. F. Talbot, T. Matsuura and S. Sourirajan 1981 in Synthetic membranes, vol. II, A. F. Turbak, ed. ACS Symposium Series, Wash. D.C.

Fontell, K., A. Ceglie, B. Lindman and B. W. Ninham 1986 Acta Chem. Scand. A40, 247.

Fontell, K. and B. Lindman 1983 J. Phys. Chem. 87, 3289.

Gallo, R. C. 1987 Scientific American, Jan. 1987.

Guering, P. and B. Lindman 1985 Langmuir ****.

Hasegawa, H. 1986 Personal communication.

Hasegawa, H., H. Tanaka, K. Yamasaki and T. Hashimoto (submitted to Macromolecules).

Hosemann, R. and N. Bagchi 1962 Direct analysis of diffraction by matter, North-Holland Pub., Amsterdam.

Huq, R., D. Frydrych and G. C. Farrington 1983 in Proceedings of the symposium on membranes and ionic and electronic conducting polymers, May 17–19, 1982 Case Western Reserve University, The Electrochemical Society, N.J.

Hyde, S. T., S. Andersson, B. Ericsson and K. Larson 1984 Z. Krist. 168, 213.

Inoue, T., T. Soen, T. Hashimoto and H. Kawai 1968 Presentation at the International Symposium on Macromolecular Chemistry, Toronto, Canada, Sep. 5, 1968.

Ishii, K., S. Konomi, M. Kai, N. Ukai and N. Uno 1981 in Synthetic membranes, vol. II, A. F. Turbak, ed. ACS Symposium Series, Wash. D.C.

Jacobs, P. A., N. I. Jaeger, P. Jiru and G. Schulz-Ekloff eds. 1982 Metal microstructures in zeolites, proceedings of Bremen Workshop of Sep. 22–24, 1982. Elsevier Scientific Pub. Co., Amsterdam.

Kai, M., K. Ishii, Z. Honda, H. Tsugawa, M. Maekawa, T. Kishimoto and S. Yamagama 1981 in Synthetic membranes, vol. II, A. F. Turbak, ed. ACS Symposium Series, Wash. D.C.

Kedem, O. and Z. Bar-On 1986 in Industrial membrane processes, AIChE Symposium Series 248, 82, 19.

Kesting, R. E. 1985 Synthetic polymeric membranes, John Wiley and Sons.

Kilpatrick, P. K. 1983 Ph. D. thesis, Univ. of Minn.

Kirk, G. L. and S. M. Gruner 1985 J. Physique 46, 761.

Klibanov, A. 1987 "Enzymatic processes in organic solvents", presentation at U. Mass. Amherst, Feb. 20, 1986.

Kost, Y. 1987 "Internally and externally-controlled drug-release membranes", presentation at U. Mass. Amherst, Jan. 15, 1987.

Kraus, K., A. Schor and J. Johnson 1967 Desalination 1, 225.

Larsson, K. 1967 Z. Phys. Chem. (Frankfurt am Main) 56, 173.

Leibler, L. 1980 Macromolecules 13, 1602.

Lindman, B. 1986 Private communication.

Lindblom, G., K. Larsson, L. Johansson, K. Fontell and S. Forsen 1979 J. Am. Chem. Soc. 101 (19), 5465.

Longley, W. and T. J. McIntosh 1983 Nature 303, 612.

Lundsted, L. G. and I. R. Schmolka 1976 in Block and Graft Copolymerization, vol. II, R. J. Ceresa, ed., John Wiley and Sons, N.Y.

Luzzati, V. and P. A. Spegt 1967 Nature 215, 701.

Luzzati, V., A. Tardieu, T. Gulik-Krzywicki, E. Rivas and F. Reiss-Husson 1968 Nature 220, 485.

Luzzati, V., A. Tardieu and T. Gulik-Krzywicki 1968 Nature 217, 1028.

Mitchell, D. J., G. J. T. Tiddy, L. Waring, T. Bostock and M. P. McDonald 1983 J. Chem. Soc. Faraday I 79, 975.

Mori, K., H. Hasegawa, and T. Hashimoto 1985 Polymer J. 17, 799.

Nilsson, P.-G. 1984 Ph. D. thesis, Lund Univ.

Ninham, B. W., S. J. Chen and D. F. Evans 1984 J. Phys. Chem. 88, 5855.

Nitsche, J. C. C. 1985 Arch. Rat. Mech. Anal. 89, 1 (see 'added in proof').

Ohta, T. and K. Kawasaki 1986 Macromolecules 19, 2621.

Pistoia, G. and O. Bagnerelli 1979 J. Polym. Sci. Polym. Chem. Ed. 17, 1001.

Raistrick, J. 1982 Proceedings of the World Filtration Congress III, London.

Rilfors, L., P.-O. Eriksson, G. Arvidson and G. Lindblom 1986 Biochemistry 25 (24), 7702.

Sakai, Y., H. Tsukamoto, Y. Fryii and H. Tanzawa 1980 in Ultrafiltration membranes and applications, A. Cooper, ed., Plenum, N.Y.

Schechtman, L. and M. E. Kenney 1983 in Proceedings of the symposium on membranes and ionic and electronic conducting polymers, May 17–19, 1982 Case Western Reserve University, The Electrochemical Society, N.J.

Schlogl, R. 1955 Z. Phys. Chem. (Frankfurt) 3, 73.

Schoen, A. 1970 Nasa Technical Note TN D-5541.

Schwarz, H. A. 1890 Gesammelte mathematische Abhandlungen, Springer, Berlin, 2 vols.

Scriven, L. E. 1976 Nature 263, 123. See also Scriven, L. E. 1977 in Micellization, solubilization, and microemulsions, ed. K. L. Mittal, vol. 2, Plenum Press, N.Y., 877.

Smith, K., W. Babcock, R. Baker and M. Conrad 1981 in Chemistry and water reuse, W. Cooper, ed., Ann Arbor Science Pub., Ann Arbor, Mich.

Sollner, K. 1932 Z. Elektrochem. 83, 274.

Sollner, K. 1930 Z. Elektrochem. 36, 234.

Spatz, D. D. 1981 in Synthetic membranes, vol. II, A. F. Turbak, ed. ACS Symposium Series, Wash. D.C.

Spegt, P. A. 1964 Ph. D. thesis, Univ. Strasbourg.

Surlyn Ionomers, E. I. DuPont de Nemours, Wilmington, Del.

Thomas, E. L., D. B. Alward, D. J. Kinning, D. C. Martin, D. L. Handlin, Jr. and L. J. Fetters 1986 Macromolecules 19 (8), 2197.

Vaughn, T. H., H. R. Suter, L. G. Lunsted and M. G. Kramer 1951 J. Am. Oil Chemists' Soc. 28, 294.

Ward, W. 1972 in Recent developments in separation science, N. Li, ed., vol. I, CRC Press, Boca Raton, Fla.

Winsor, P. A. 1974 in Liquid crystals and plastic crystals, vol. 1, G. W. Gray and P. A. Winsor eds, Ellis Harwood Ltd., Chichester.

Zadsadsinski, J. A. 1985 Ph. D. Thesis, Univ. of Minnesota.

I claim:

1. A process of making a stabilized triply periodic porous material with a uniform pore size in which the pores bodies and pore throats are substantially identical in size and shape, comprising the steps of:
    (a) distilling a mixture of methylmethacrylate and azoisobutyronitrile;
    (b) mixing the product of (a) with a quantity of didodecyldimethyl ammonium bromide;
    (c) adding a solvent to the mixture of (b);
    (d) stirring the mixture of (c) until a viscous isotropic phase is formed;
    (e) equilibrating said viscous isotropic phase for at least one week; and
    (f) irradiating said equilibrated isotropic phase to cause radical chain polymerization of the methylmethacrylate and formation of a stabilized triply periodic porous material with uniform pore size in which the pore size bodies and pore size throats are substantially identical in size and shape.

2. A process as recited in claim 1, wherein the distillate is a mixture of at least 10% of methylmethacrylate at least 55% didodecyldimethyl ammonium bromide and 0.004 milligrams per milliliters of azoisobutyronitrile.

3. A process as recited in claim 2, wherein said solvent is a mixture of at least 35% water.

4. A process of making a stabilized triply periodic porous material with a uniform pore size in which the pore size bodies and pore size throats are substantially identical in size and shape, comprising the steps of:
    (a) distilling an oleic compound mixed with a free radical source;
    (b) mixing the product of (a) with a quantity of surfactant;
    (c) adding a solvent aliquot to the mixture of (b);
    (d) stirring the mixture of (c) until a viscous isotropic phase is formed;
    (e) equilibrating said viscous isotropic phase; and
    (f) providing a free radical initiator to said equilibrated viscous isotropic phase causing radical chain polymerization of said oleic compound by the decomposition of said free radical source and the formation of a stabilized triply periodic microporous material with uniform pore size in which the pore size bodies and pore size throats are substantially identical in size and shape.

5. A process as recited in claim 4, wherein said oleic compound is a hydrocarbon.

6. A process as recited in claim 5, wherein said hydrocarbon is aliphatic.

7. A process as recited in claim 4, wherein said surfactant is anionic.

8. A process as recited in claim 4, wherein said surfactant is cationic.

9. A process as recited in claim 4, wherein said free radical initiator is selected from the group consisting of:
    (a) ultra violet light;
    (b) thermal decomposition; and
    (c) equivalents.

* * * * *